United States Patent
Gadagkar et al.

(10) Patent No.: US 10,279,186 B2
(45) Date of Patent: *May 7, 2019

(54) AUTOMATED VERIFICATION OF MRI COMPATIBILITY OF ACTIVE IMPLANTABLE MEDICAL DEVICE

(71) Applicant: Medtronic, Inc., Minneapolis, MN (US)

(72) Inventors: Hrishikesh Gadagkar, Plymouth, MN (US); James Zimmerman, Blaine, MN (US); James M. Olsen, Plymouth, MN (US); Robyn L. Jagler, Eagan, MN (US); Timothy R. Abraham, Lino Lakes, MN (US); Jeffrey R. Dixon, Chesterfield, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,401

(22) Filed: Jun. 25, 2018

(65) Prior Publication Data

US 2018/0304087 A1 Oct. 25, 2018

Related U.S. Application Data

(63) Continuation of application No. 15/630,661, filed on Jun. 22, 2017, now Pat. No. 10,004,910, which is a (Continued)

(51) Int. Cl.
*A61N 1/37* (2006.01)
*A61N 1/372* (2006.01)
(Continued)

(52) U.S. Cl.
CPC .......... *A61N 1/37264* (2013.01); *A61B 5/055* (2013.01); *A61N 1/372* (2013.01);
(Continued)

(58) Field of Classification Search
CPC .......................... A61N 1/37252; A61N 1/3718
(Continued)

(56) References Cited

U.S. PATENT DOCUMENTS

| 4,951,672 A | 8/1990 | Bushwald et al. |
| 7,082,328 B2 | 7/2006 | Funke |

(Continued)

FOREIGN PATENT DOCUMENTS

| WO | 2006055582 A2 | 5/2006 |
| WO | 2008029001 A1 | 3/2008 |

(Continued)

OTHER PUBLICATIONS

"Medtronic Starts Study of MRI Compatible Pacemaker," MedGadget Internet Journal of Emerging Medical Technologies, medgadget.com, Feb. 13, 2007, 2 pp.

(Continued)

*Primary Examiner* — Nadia A Mahmood
(74) *Attorney, Agent, or Firm* — Shumaker & Sieffert, P.A.

(57) ABSTRACT

A system may include a processor configured to automatically obtain magnetic resonance imaging compatibility information relating to compatibility of an active implantable medical device implantable in a patient with an MRI modality from at least two information sources. The processor may also be configured to automatically determine compatibility of the active implantable medical device with the magnetic resonance imaging modality based on the magnetic resonance imaging compatibility information.

24 Claims, 8 Drawing Sheets

Related U.S. Application Data continuation of application No. 12/626,342, filed on Nov. 25, 2009, now Pat. No. 9,694,188.

(60) Provisional application No. 61/118,342, filed on Nov. 26, 2008.

(51) Int. Cl.
| | |
|---|---|
| *A61B 5/055* | (2006.01) |
| *G01R 33/28* | (2006.01) |
| *A61N 1/39* | (2006.01) |
| *G16H 40/40* | (2018.01) |
| *G06F 19/00* | (2018.01) |
| *A61N 1/08* | (2006.01) |

(52) U.S. Cl.
CPC .......... *A61N 1/3718* (2013.01); *A61N 1/3925* (2013.01); *G01R 33/285* (2013.01); *G06F 19/00* (2013.01); *G16H 40/40* (2018.01); *A61N 1/086* (2017.08); *A61N 1/37247* (2013.01); *A61N 1/37258* (2013.01); *A61N 1/37282* (2013.01); *G01R 33/288* (2013.01)

(58) Field of Classification Search
USPC .......................................................... 607/60
See application file for complete search history.

(56) References Cited

U.S. PATENT DOCUMENTS

| | | | |
|---|---|---|---|
| 7,561,915 | B1 | 7/2009 | Cooke et al. |
| 8,712,540 | B2 | 4/2014 | Gadagkar et al. |
| 8,721,695 | B2 | 5/2014 | Tass et al. |
| 9,174,059 | B2 | 11/2015 | Gadagkar et al. |
| 9,694,188 | B2 | 7/2017 | Gadagkar et al. |
| 10,004,910 | B2 | 6/2018 | Gadagkar et al. |
| 2002/0111754 | A1 | 8/2002 | Lange et al. |
| 2005/0027191 | A1 | 2/2005 | Uutela et al. |
| 2005/0258242 | A1 | 11/2005 | Zarembo |
| 2006/0167496 | A1 | 7/2006 | Nelson et al. |
| 2006/0247509 | A1 | 11/2006 | Tuccillo et al. |
| 2006/0293591 | A1 | 12/2006 | Wahlstrand et al. |
| 2007/0100232 | A1 | 10/2007 | Hiller et al. |
| 2007/0244524 | A1 | 10/2007 | Qu et al. |
| 2007/0255332 | A1 | 11/2007 | Cabelka et al. |
| 2008/0046286 | A1 | 2/2008 | Halsted |
| 2008/0242944 | A1 | 10/2008 | Sharma |
| 2009/0054954 | A1 | 2/2009 | Foley et al. |
| 2009/0054955 | A1 | 4/2009 | Kopell et al. |
| 2009/0088680 | A1 | 4/2009 | Aravanis et al. |
| 2010/0137945 | A1 | 6/2010 | Gadagkar et al. |
| 2010/0137946 | A1 | 6/2010 | Gadagkar et al. |

FOREIGN PATENT DOCUMENTS

| | | |
|---|---|---|
| WO | 2008089003 A2 | 7/2008 |
| WO | 2009155371 A1 | 12/2009 |

OTHER PUBLICATIONS

Waknine, "MRI Can Cause Serious Injury in Patients With Implanted Neurostimulators," Medscape Today from WebMD, May 11, 2005, 2 pp.

International Search Report and Written Opinion from International Patent Application No. PCT/US2009/065964, dated Jun. 29, 2010, 14 pp.

International Preliminary Report on Patentability from International Patent Application No. PCT/U2009/065964, dated Jun. 9, 2011, 8 pp.

International Search Report and Written Opinion from International Application No. PCT/US2009/065974, dated Aug. 27, 2010, 13 pp.

International Preliminary Report on Patentability from International Application No. PCT/US2009/065974, dated Jun. 9, 2011, 7 pp.

Shellock R & D Services, Inc., "Screening Patients for MR Procedures and Individuals for the MR Environment," MRisafety.com, downloaded Nov. 26, 2008, 6 pp. (Current Protocols in Magnetic Resonance Imaging, Supplement 11, John Wiley and Sons, Publishers, 2003).

Shellock R & D Services, Inc., "Cardiac Pacemaker: EnRhythm MRI SureScan Pacing System," MRISafety.com, downloaded Jan. 12, 2010, 2 pp.

Medtronic, Inc, "FDA Grants Medtronic Approval to Begin Clinical Trial of First Pacemaker System Designed for Safe Use in MRI Machines," Jan. 28, 2008, 5 pp.

Medtronic, Inc., "MRI procedural information for EnRhythm MRI™ SureScan™ Pacing System," 2008, 18 pp.

Prosecution History from U.S. Appl. No. 12/626,342, dated Jun. 21, 2011 through Apr. 4, 2017, 271 pp.

Prosecution History from U.S. Appl. No. 15/630,661, dated Jun. 29, 2017 through Feb. 27, 2018, 21 pp.

Prosecution History from U.S. Appl. No. 12/626,354, dated Jun. 21, 201 through Dec. 16, 2015, 81 pp.

Prosecution History from U.S. Appl. No. 12/626,374, dated Jul. 13, 2011 through Mar. 5, 2014, 161 pp.

Prosecution History from U.S. Appl. No. 14/251,246, dated Jul. 8, 2014 through Sep. 18, 2015, 53 pp.

AUTOMATED VERIFICATION OF MRI COMPATIBILITY OF ACTIVE IMPLANTABLE MEDICAL DEVICE

This application is a continuation of U.S. patent application Ser. No. 15/630,661, filed Jun. 22, 2017, which will issue as U.S. patent Ser. No. 10/004,910 on Jun. 26, 2018, which is a continuation of U.S. patent application Ser. No. 12/626,342, filed Nov. 25, 2009, now U.S. Pat. No. 9,694,188, which claims the benefit of U.S. Provisional Application No. 61/118,342, entitled "VERIFICATION OF MRI COMPATIBILITY OF ACTIVE IMPLANTABLE MEDICAL DEVICE," and filed on Nov. 26, 2008. The entire contents of each of these applications are incorporated herein by reference.

TECHNICAL FIELD

The disclosure relates to implantable medical devices and, more particularly, to magnetic resonance imaging (MRI) compatibility of implantable medical devices.

BACKGROUND

Implantable medical devices may be used to deliver therapy to patients to treat a variety of symptoms or conditions such as chronic pain, tremor, Parkinson's disease, epilepsy, depression, urinary or fecal incontinence, sexual dysfunction, obesity, or gastroparesis. For example, an implantable medical device may deliver neurostimulation therapy via leads that include electrodes located proximate to the spinal cord, pelvic nerves, peripheral nerves, the stomach or other gastrointestinal organs, or within the brain of a patient. Other examples of implantable medical devices include implantable medical devices configured to deliver electrical stimulation for cardiac therapy, such as cardiac pacing, cardioversion/defibrillation, resynchronization, or the like.

In general, an implantable medical device may deliver electrical stimulation therapy in the form of electrical signals such as pulses or other waveforms via one or more electrodes carried by one or more implantable leads. Many implantable medical devices include metallic components, such as a housing, conductors, electrodes, and the like. For some implantable medical devices, these metallic components may make a magnetic resonance imaging (MRI) procedure undesirable. For example, MRI imaging produces radio frequency (RF) energy that may interact with some of the metallic components of the implanted medical device.

SUMMARY

In general, the disclosure is directed to techniques for determining whether a patient having an active implantable medical device (AIMD) implanted in his or her body is a candidate for an MRI scan. The techniques may include determining whether the AIMD is compatible with an MRI scan. For example, the AIMD may be compatible with an MRI modality having particular characteristics such as, for example, a certain magnetic field strength.

In one aspect, the disclosure is directed to a system comprising a processor configured to automatically obtain MRI compatibility information relating to compatibility of an AIMD implantable in a patient with an MRI modality from at least two information sources. According to this aspect of the invention, the processor is also configured to automatically determine compatibility of the AIMD with the MRI modality based on the MRI compatibility information.

In another aspect, the disclosure is directed to a method comprising automatically obtaining with a processor MRI compatibility information relating to compatibility of an AIMD implantable in a patient with an MRI modality from at least two information sources. According to this aspect of the disclosure, the method further includes automatically determining with the processor compatibility of the AIMD with the MRI modality based on the MRI compatibility information.

In an additional aspect, the disclosure is directed to a computer-readable medium comprising instructions that cause a processor to automatically obtain MRI compatibility information relating to compatibility of an AIMD implantable in a patient with an MRI modality from at least two information sources. According to this aspect of the disclosure, the computer-readable medium also comprises instructions that cause the processor to automatically determine compatibility of the AIMD with the MRI modality based on the MRI compatibility information.

In another aspect, the disclosure is directed to a system comprising a processor configured to automatically obtain MRI compatibility information relating to compatibility of an AIMD implantable in a patient with an MRI modality from an external data server. According to this aspect of the disclosure, the processor is configured to automatically determine compatibility of the AIMD with the MRI modality based on the MRI compatibility information.

In an additional aspect, the disclosure is directed to a method including automatically obtaining with a processor MRI compatibility information relating to compatibility of an AIMD implantable in a patient with an MRI modality from an external data server. According to this aspect of the disclosure, the method also includes automatically determining with the processor compatibility of the AIMD with the MRI modality based on the MRI compatibility information.

In a further aspect, the disclosure is directed to a system comprising a patient information terminal that receives MRI compatibility information from a patient. The MRI compatibility information comprises information relating to compatibility of an AIMD implantable in the patient and an MRI modality. According to this aspect of the disclosure, the system also includes a processor that automatically determines compatibility of the AIMD with the MRI modality based on the MRI compatibility information.

In another aspect, the disclosure is directed to a method that includes receiving MRI compatibility information from a patient via a patient information terminal. The MRI compatibility information comprises information relating to compatibility of an AIMD implantable in the patient and an MRI modality. According to this aspect of the disclosure, the method also includes automatically determining, with a processor, compatibility of the AIMD with the MRI modality based on the MRI compatibility information.

In an additional aspect, the disclosure is directed to a computer-readable medium comprising instructions that cause a processor to receive MRI compatibility information from a patient via a patient information terminal. The MRI compatibility information comprises information relating to compatibility of an AIMD implantable in the patient and an MRI modality. According to this aspect of the disclosure, computer-readable medium also comprises instructions that cause the processor to automatically determine compatibility of the AIMD with the MRI modality based on the MRI compatibility information.

In another aspect, the disclosure is directed to a system including an AIMD implantable in a body of a patient and a patient programmer for the AIMD. According to this aspect of the disclosure, the patient programmer is configured to obtain MRI compatibility information relating to compatibility of the AIMD with an MRI modality.

In a further aspect, the disclosure is directed to a method comprising obtaining from at least one of a memory of a patient programmer or a memory of an active implantable medical device (AIMD), via a patient programmer, magnetic resonance imaging (MRI) compatibility information relating to compatibility of an active implantable medical device (AIMD) with an MRI modality.

In another aspect, the disclosure is directed to a computer-readable medium comprising instructions that cause a processor to obtain from at least one of a memory of a patient programmer or a memory of an active implantable medical device (AIMD), via a patient programmer, magnetic resonance imaging (MRI) compatibility information relating to compatibility of an active implantable medical device (AIMD) with an MRI modality.

In some examples, the techniques described in this disclosure may be performed using instructions stored on a computer readable medium that cause a processor to perform the techniques.

The details of one or more examples are set forth in the accompanying drawings and the description below. Other features, objects, and advantages of the disclosure will be apparent from the description and drawings, and from the claims.

DETAILED DESCRIPTION

Figure 1:
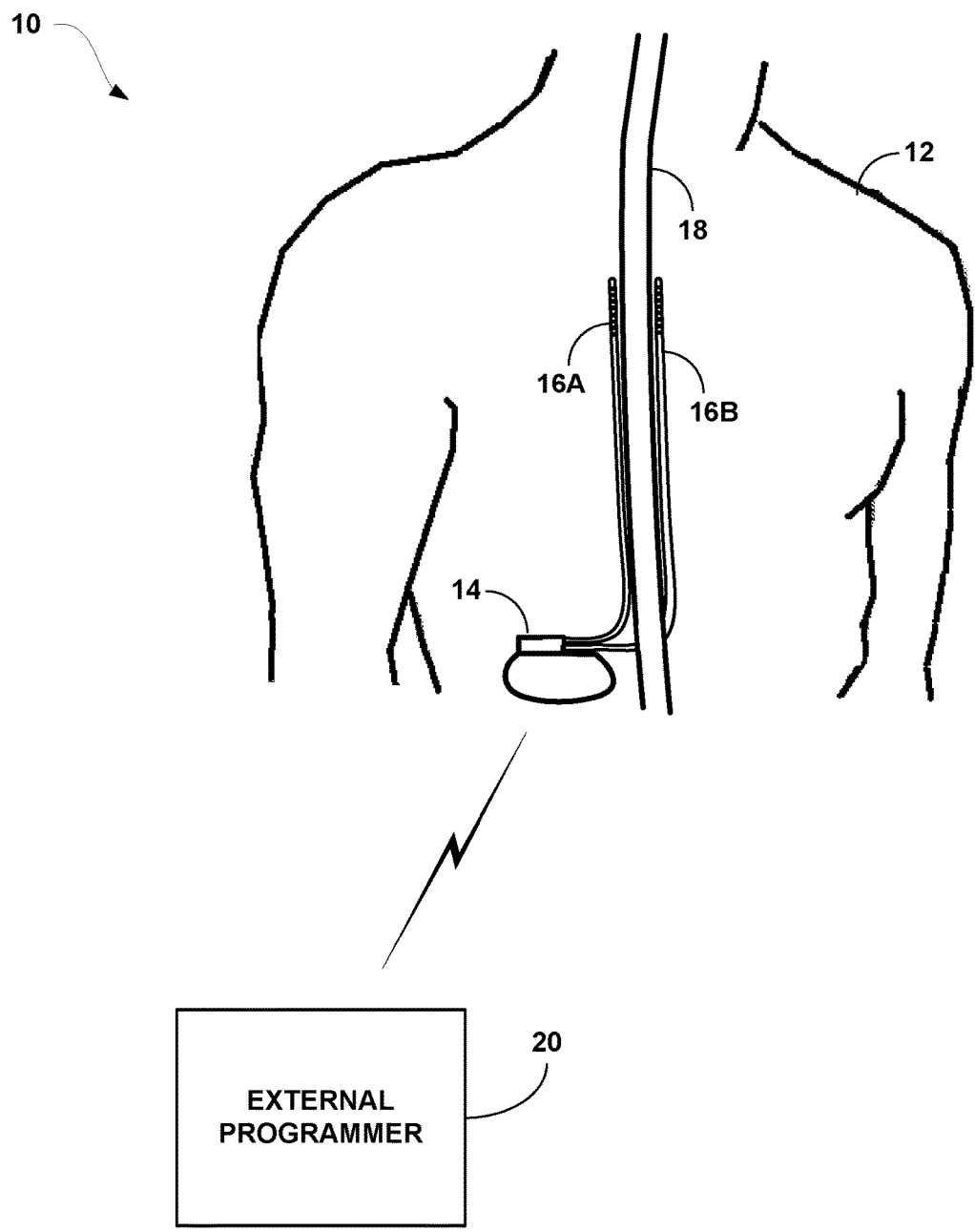
FIG. 1 is a schematic diagram illustrating a system including an implantable medical device in the form of an implantable electrical stimulation system.

In general, the disclosure is directed to techniques for determining whether a patient, and, more particularly, a patient having an active implantable medical device (AIMD) implanted in his or her body, is a candidate for an MRI scan. The techniques may include determining whether the AIMD is compatible with an MRI scan performed by a particular type or class of MRI modality, or with particular settings of the MRI modality, that would be used to perform the MRI scan on the patient. For example, the AIMD may be compatible with an MRI modality having particular characteristics such as, for example, a certain magnetic field strength or a magnetic field strength below a particular threshold value. The techniques described in this disclosure, in some examples, may include collecting data regarding the AIMD, the compatibility of the AIMD with a particular MRI modality, operating parameters of the MRI modality, and the like. In some examples, the techniques also may include determining, based on the collected data, whether the AIMD is compatible with the MRI modality.

In some examples, the techniques described in this disclosure may be computer-implemented in a computer device or system. As an example, the techniques may be implemented via a computer user interface that guides a user to collect pertinent information. For example, the user may be a patient in which the AIMD is implanted. Additionally or alternatively, the computer device or system may be configured to automatically store and retrieve information that is relevant or useful in an MRI compatibility determination for the patient. In some examples, the computer user interface may be realized at least in part by one or more computer-implemented media, executed by a processor, such as one or more interactive web pages presented by a web server and displayed to a user. The web pages may be configured to prompt a user, such as the patient, a clinician, a medical technician, or the like, to enter information regarding the AIMD and, optionally, the MRI modality, or to retrieve the information from one or more servers or devices, which may be local or remote from the device that presents the computer user interface.

In other examples, the techniques described in this disclosure may be implemented at least in part using written materials such as a poster or instruction sheet that provides graphical and/or textual information to guide a user, such as a patient, clinician (e.g., a radiologist, referring physician, managing physician, or implanting physician), medical technician, MRI staff member, MRI facility scheduler, nurse, or the like to gather the pertinent information regarding the AIMD and MRI modality. The written materials may be stored as computer-readable media and presented in soft copy form on a computer display. In some cases, the written materials may be interactive in the sense that the patient may enter information, manipulate check boxes, advance through a menu or series of user interface screens, or the like, to complete the process outlined by the written materials. In some cases, the written materials may be a series of web pages that guide the user through the process, and permit entry of pertinent information. In other cases, the written materials may be hard copy forms that are used by the user during the MRI compatibility determination process. The use of a poster, instruction sheet or other written materials may be combined with computer-implemented media and methods for collecting, storing, and retrieving pertinent information. Hence, in some examples, the MRI compatibility determination techniques described in this disclosure may be performed in a hybrid system that includes both written materials and computer-implemented media.

An AIMD may be an active IMD (AIMD), for example, in the sense that it is electrically powered or controlled. AIMDs may include a variety of different types of devices such as, for example, neurostimulators, cardiac rhythm management devices, drug delivery devices, physiological parameter monitoring devices, fluid control devices such as a cerebral spinal fluid (CSF) shunts or valve devices, mechanical urinary or fecal incontinence devices, mechanical sexual dysfunction therapy devices, or the like. In general, an electrical stimulation device in the form of a neurostimulator will be described for purposes of illustration.

In some examples, an AIMD may not be compatible with an MRI scan. For example, the magnetic field produced by an MRI modality during the MRI scan may induce a current or voltage in conductive portions of the AIMD. The induced current or voltage may cause electrically resistive and thermally conductive portions of the AIMD to increase in temperature, which could cause undesirable heating in tissue adjacent to the AIMD or could interfere with operation of the AIMD. In other cases, a magnetic field produced by the MRI scan may cause one or more components of an AIMD to move from a normally implanted position. In these examples, it may be desirable to determine whether the AIMD implanted in the patient is compatible with the MRI scan such that it is not susceptible to the issues described above. Hence, compatibility of the AIMD with a particular MRI modality may refer to whether the AIMD is constructed such that it does not produce an undesired level of heating or such that it maintains at least limited operation in the presence of an MRI field produced by the modality.

However, in other examples, an AIMD may include one or more features that facilitate compatibility with MRI modalities that produce certain magnetic field strengths or magnetic field strengths below a threshold value. For example, some AIMDs may be constructed with MRI safe (MRIS) or MRI conditionally safe (MRICS) hardware. MRIS hardware includes hardware that is confirmed to be safe when used with substantially any MRI modalities operating with substantially any operating characteristics. In contrast, MRICS hardware includes hardware that is confirmed to be safe when used with certain, predetermined MRI modalities or certain, predetermined MRI scan parameters. In some examples, MRICS or MRIS hardware may include lead conductor configurations that produce less heat in the presence of MRI energy, particularly when MRI energy is less than a prescribed level. MRICS or MRIS hardware also may include a thermally insulated outer housing of the AIMD, which may reduce undesirable heating of tissue adjacent to the outer housing. In each case, it may be important to verify MRICS or MRIS status for an AIMD implanted in a patient before exposing the patient to energy from an MRI modality.

As an illustration with or without MRIS or MRICS hardware, some AIMDs, for example, may be compatible with an MRI modality that produces a magnetic field having a certain magnitude. As an example, some AIMDs may be compatible with MRI modalities that produce an MRI scan magnetic field strength equal to approximately 1.5 Tesla (T). In these examples, the techniques described in this disclosure may include identifying the AIMD as an AIMD that is compatible with an MRI scan that has a magnetic field with a certain magnitude, and identifying the MRI modality as producing a magnetic field having a certain magnitude. In some examples, other operating parameters of an MRI modality may be identified and utilized to determine compatibility between an AIMD and an MRI modality. For example, some AIMDs may be compatible with an MRI modality that produces a magnetic field having a maximum magnitude that is less than a threshold value. In such examples, the techniques for determining compatibility between the AIMD and an MRI modality may include identifying the AIMD as an AIMD that is compatible with an MRI scan that has a magnetic field with a maximum magnitude lower than a threshold value, and identifying the MRI modality as producing a magnetic field having a maximum magnitude less than the threshold value. As another example, some AIMDs may be compatible with an MRI modality that produces a specific absorption rate (SAR) of less than a threshold value, such as, for example, 2.0 W/kg. In such examples, the techniques for determining compatibility between the AIMD and an MRI modality may include identifying the AIMD as an AIMD that is compatible with an MRI modality that produces a SAR lower than a threshold value, and identifying the MRI modality as producing a SAR that is less than the threshold value.

In some examples, the techniques for determining whether a patient having a medical device implanted in his or her body is a candidate for an MRI scan may optionally include confirming that the AIMD is or is not compatible with the MRI modality by determining the type of hardware and/or software of the AIMD. The techniques described in this disclosure also may optionally include determining a location in the patient at which the AIMD is implanted. In some examples, the techniques may further optionally include testing the electrical impedance of one or more leads (and/or lead extensions or lead adaptors, if present) that may be coupled to the AIMD to determine whether any of the leads are damaged, which may cause the patient to not qualify for an MRI scan due to increased risk.

In some examples, the AIMD may include an MRI conditionally safe operating mode, and the techniques described in this disclosure may include configuring the AIMD in the MRI conditionally safe operating mode. In some examples, the MRI conditionally safe operating mode may cause the AIMD to suspend therapy delivery, but may maintain the AIMD in a low power state so that the AIMD does not accidentally deliver therapy to the patient during the MRI scan.

In some examples, the techniques may further include interrogating the MRI modality and determining whether the MRI modality is in the proper operating mode and the MRI scan parameters are safe for the AIMD. The techniques described in this disclosure may also include commencing the MRI scan when it is determined that the AIMD is compatible with the MRI modality. In some examples, the results of the techniques, e.g., the collected MRI compatibility information and/or decisions made based on the information, may be archived in a database or output by a computer to enable documentation of performance of the technique and the results of the technique. For example, it may be desirable to maintain a record indicating that the compatibility determination technique was performed. In some cases, the record may indicate the scope of issues that were considered and/or the number of tasks that were performed.

Some aspects of the techniques described in this disclosure may be performed using instructions stored on a computer-readable medium and executed by one or more processors to carry out such techniques in conjunction with a computing system. Some aspects may be implemented in part by written materials such as a poster or instruction sheet utilized by a user to collect and/or record the pertinent information. Instructions executed by the processor may comprise software associated with an application program running on a computer or data server or associated with one or more web pages presented on a computer and obtained from a web server. In either case, the software may present a graphical user interface to guide a user, such as a patient, clinician, medical technician, or the like to enter any of a variety of pertinent information to support the MRI compatibility determination.

In some examples, the instructions may cause the processor to retrieve at least some of the pertinent data from one or more devices, such as the AIMD, a patient information terminal, a patient programmer, or one or more data servers. In some examples, at least one of the one or more devices may be external to the device that includes the processor. In addition, some of the devices, such as data servers, may be remote from the device that includes the processor. One or more data servers may be maintained by the facility at which the MRI modality is located, by a manufacturer of the MRI modality, by a manufacturer of the AIMD, or by a third party, such as a third party that maintains compatibility information and/or relevant design specification information for various MRI modalities and various AIMDs. In some examples, a software application program or web page may be accessed on a computing device that is connected to a network. Network access may facilitate entry of different portions of the pertinent data by different users, or at different devices, as well as sharing of information among different devices and users. In some examples, a processor may automatically retrieve MRI compatibility information from at least one information source that is external from the device in which the processor is included. For example, the processor may be contained in a patient or clinician programmer, and may automatically retrieve information from the AIMD, a patient information terminal, another programmer, and/or one or more data servers, some of which may be remote in the sense that they are located at a different location than the processor and accessed remotely over a network. In some examples, a processor may automatically retrieve MRI compatibility information from at least two information sources, e.g., the AIMD, the patient information terminal, the patient programmer, and/or one or more data servers, and at least one of the information sources may or may not be a device in which the processor is included. The MRI compatibility information may include information regarding an AIMD (AIMD information) and/or information regarding an MRI modality (MRI modality information).

In some examples, the patient may enter and/or retrieve some information via a patient information terminal. The patient information terminal may include, for example, a computer executing a software program or accessing a website, into which the patient may enter and/or from which the patient may retrieve MRI compatibility information prior to arriving at the MRI facility. In other examples, the patient information terminal may include a computer at the MRI facility that executes a software program or accesses a website into which the patient may enter and/or from which the patient may retrieve MRI compatibility information. In other examples, a staff member of the MRI facility may enter and/or retrieve some information during registration of the patient at a computing device associated with the MRI facility, e.g., based on information obtained from the patient over the telephone, or over other electronic communication media, such as email, web chat, video teleconference, or the like. Hence, the patient information terminal may be located at the MRI facility or elsewhere, or presented by a web page or other computer interface presented by a computing device at a location remote from the MRI facility. In some examples, an MRI technician may enter and/or retrieve some of the information at a computing device associated with the MRI modality. A clinical record keeper may enter and/or retrieve some of the information at another computing device, e.g., to verify that the compatibility determination was performed or performed properly.

One or more processors associated with one or more computing devices may automatically determine whether the patient has an AIMD implanted in his or her body that is compatible with the MRI modality utilized at the MRI facility based on the collective information retrieved by the processor(s) or entered by users, such as the patient, the staff member, and/or the MRI technician. Alternatively, one or more processors associated with one or more computing devices may present information based on the information entered by various persons for verification by a user to determine whether the patient has an AIMD implanted in his or her body that is compatible with the MRI modality utilized at the MRI facility. Hence, the actual compatibility determination may be made automatically by one or more computing devices without user intervention, may be rendered by a human user, or the computing system may generate a recommended compatibility determination for review and approval by a human user.

In other examples, the techniques described in this disclosure may be performed at least in part using a poster or instruction sheet that guides a user through the process of collecting the pertinent information. For example, an instruction sheet may be followed by a patient to provide the pertinent information. As other examples, the instruction sheet may be utilized by an MRI technician or other staff person of the MRI facility to collect pertinent information from a variety of sources. The instruction sheet may further provide criteria that enable the user to determine whether the AIMD implanted in the patient is compatible with the MRI modality utilized by the MRI facility.

The sources of information may include, for example, the patient, a patient ID card, AIMD compatibility documentation, a manufacturer website, interaction with or information from a manufacturer employee, an MRI modality, a patient programmer or clinician programmer, interaction with or information from the patient's primary physician, information carried by the AIMD, or information stored by one or more data servers (e.g., an MRI data server, and AIMD data server, or the like). Information carried by the patient programmer, clinician programmer, or AIMD may include electronic data indicating whether the AIMD is MRI compatible or conditionally MRI compatible, or may include data that can be used to determine whether the AIMD is MRI compatible.

For example, the electronic data may be stored in memory in the programmer or AIMD and specify a manufacturer, model name or number, pertinent MRI compatibility specifications, or other information. Such electronic data may be obtained by wired or wireless communication with the programmers or the AIMD. In some cases, the AIMD may further include radio-opaque markers or codes that can be imaged, e.g., by fluoroscopy, to determine information similar to that described above.

In some examples, a patient programmer may be utilized by a patient or another user, such as a MRI technician, to interrogate an AIMD implanted in the patient to retrieve information carried by the AIMD that is pertinent to compatibility of the AIMD with an MRI modality. The information may be stored in memory of the AIMD, and may have been programmed into memory of the AIMD at the time of implant, after gathering of the MRI compatibility information by a device or system described in this disclosure, or after a change to the AIMD or another device implanted in the patient (e.g., after an impedance measurement indicates a lead failure). The patient programmer may retrieve the MRI compatibility information from the AIMD upon receiving a command from the user to retrieve the MRI compatibility information or upon receiving a command from the user to determine whether the AIMD is MRI compatible.

Upon receiving such a command, the patient programmer may automatically retrieve the MRI compatibility information from the AIMD. In some examples, the patient programmer may display the MRI compatibility information to the user to allow the user to determine whether the AIMD is compatible with the MRI modality. In other examples, the patient programmer may automatically determine, based on the MRI compatibility information, whether the AIMD is compatible with the MRI modality and display the result to the user for verification, e.g., via a display associated with the programmer or another display that receives the result from the programmer. In some examples, the patient programmer may automatically determine, based on the MRI compatibility information, whether the AIMD is compatible with the MRI modality and, if the AIMD is compatible with the MRI modality, instruct the AIMD to enter an MRI safe operating mode. Also, in some examples, the patient programmer may be configured to communicate MRI compatibility information or a MRI compatibility determination result to another device such as a computing device used by MRI facility personnel or a computing device or controller associated with operation of the MRI modality.

As described above, the techniques described in this disclosure may be utilized to determine whether a patient having an AIMD implanted in his or her body is a candidate for an MRI scan. FIG. 1 illustrates an example patient 12 having an AIMD 14 implanted in his or her body. While patient 12 is depicted as a human being in FIG. 1, patient 12 is not necessarily a human being. For example, patient 12 may be another mammal. AIMD 14 forms one part of a medical device system 10, which also includes an external programmer 20. As shown in FIG. 1, system 10 further includes a pair stimulation leads 16A, 16B implanted within a patient 12 and coupled to AIMD 14. Stimulation leads 16A, 16B may carry one or more electrodes through which AIMD 14 delivers stimulation to a target tissue site within patient 12.

Although AIMD 14 is described in this disclosure primarily as an implantable neurostimulator, in other examples, AIMD 14 may comprise another type of therapy device or may comprise an implantable monitoring or sensing device. For example, AIMD 14 may comprise an implantable cardiac rhythm management device that delivers at least one of pacing pulses, cardioversion shocks, or defibrillation shocks to cardiac tissue of patient 12, and which may or may not monitor a cardiac rhythm of patient 12. In other examples, AIMD 14 may comprise an implantable drug delivery device or an implantable monitoring device, which monitors one or more physiological parameters of patient 12 and may or may not deliver therapy to patient 12. For examples in which the MRI compatibility determination is made or aided by a patient programmer, the patient programmer may be configured, for example, for use by a patient in selecting at least some therapy parameters or programs.

In the case of an AIMD 14 comprising an implantable neurostimulator, for example, a patient programmer may permit a patient to select particular neurostimulation therapy programs specifying parameters for delivery of neurostimulation, such as electrical stimulation voltage or current amplitude, pulse width, pulse rate, electrode configuration, duty cycle, or the like. The patient programmer may permit a patient to select individual programs, or groups of programs, or possibly adjust some of the parameters associated with the programs. In the case of an implantable drug delivery device, the patient programmer may permit a patient to select particular drug delivery programs, such as therapy schedules and associated dosage levels.

The patient programmer may be configured to permit the patient to control or adjust only a limited subset of the therapy parameters, rather than all of such therapy parameters, e.g., for safety reasons or simplicity in patient programmer operation. For example, the patient programmer may be configured to permit the patient amplitude, pulse width, or pulse rate adjustments to be made only within a limited range, or to permit only particular sets of electrode configurations to be selected by the patient. In contrast, a clinician programmer may be configured for use by a clinician or other caregiver, and permit a clinician to control or adjust a larger, and perhaps complete, set of therapy parameters, relative to the limited set of parameters adjustable via the patient programmer.

In some examples, AIMD 14 may comprise an MRI safe or an MRI conditionally safe device. An MRI safe device may include software and/or hardware features that result in AIMD 14 being compatible with substantially all MRI modalities and MRI scan parameters. An MRI conditionally safe device may include software and/or hardware features that result in AIMD 14 being compatible with a more limited range of MRI modalities and/or MRI modality scan parameters. For example, a MRI conditionally safe device may be compatible with a limited range of magnetic field power levels or MRI radio frequency (RF) coil types. In either case, hardware features may include construction of a housing of AIMD 14, leads 16, any lead extensions or lead adaptors used, and/or circuitry within AIMD 14. These hardware features may be designed to reduce or minimize inductive heating of components of AIMD 14 or leads 16 when exposed to a magnetic field generated by an MRI modality. Additionally or alternatively, the hardware or software features may be designed to reduce or minimize electromagnetic interference between the magnetic field generated by the MRI modality and operation of AIMD 14.

As shown in FIG. 1, leads 16A, 16B (collectively "leads 16") are implanted adjacent a spinal cord 18 of patient 12, e.g., for spinal cord stimulation (SCS) to alleviate pain. However, the techniques described in this disclosure are applicable to systems including an AIMD 14 coupled to leads implanted to target any of a variety of target locations within patient 12, such as leads carrying electrodes located proximate to spinal cord 18, pelvic nerves, peripheral nerves, the stomach or other gastrointestinal organs, or within the brain of a patient. In some examples, leads 16 may be coupled to lead extensions or lead adaptors.

In the example of FIG. 1, stimulation energy is delivered from AIMD 14 to spinal cord 18 of patient 12 via one or more electrodes carried by axial leads 16A and 16B implanted within the patient. In various applications, such as spinal cord stimulation (SCS), the adjacent implantable leads 16 may have longitudinal axes that are substantially parallel to one another. Various combinations of electrodes carried by the leads 16 may be used to deliver electrical stimulation, including combinations of electrodes on a single lead or combinations of electrodes on both leads. Also, in some examples, electrodes may be carried by paddle leads in which an array of electrodes may be arranged in a two-dimensional pattern, e.g., as columns or rows of electrodes, on a common planar lead surface.

For leads or other electrode arrays, electrodes may be formed as any of a variety of electrodes such as ring electrodes, segmented electrodes, needle electrodes, pad electrodes, or the like. In general, the term "electrode array" may refer to electrodes deployed on axial leads, paddle leads, or other lead configurations.

In the example of FIG. 1, leads 16 carry electrodes that are implanted adjacent to the target tissue of spinal cord 18. In particular, leads 16 may be implanted in the epidural space adjacent spinal cord 18, and coupled to AIMD 14. In the example of FIG. 1, stimulation energy may be delivered to spinal cord 18 to eliminate or reduce pain perceived by patient 12. However, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, epilepsy, urinary or fecal incontinence, sexual dysfunction, obesity, or gastroparesis. The stimulation delivered by AIMD 14 may take the form of stimulation pulses or continuous waveforms, and may be characterized by controlled voltage levels or controlled current levels, as well as pulse width and pulse rate in the case of stimulation pulses.

The stimulation energy may be delivered via selected combinations of electrodes carried by one or both of leads 16. The target tissue may be any tissue affected by electrical stimulation energy, such as electrical stimulation pulses or waveforms. Such tissue may include nerves, nerve branches, smooth muscle fiber, and skeletal muscle fiber. In the example illustrated by FIG. 1, the target tissue is spinal cord 18. Stimulation of spinal cord 18 may, for example, prevent pain signals from traveling thorough the spinal cord and to the brain of the patient. Patient 12 may perceive the interruption of pain signals as a reduction in pain and, therefore, efficacious therapy.

With reference to FIG. 1, a user, such as a clinician, physician or patient 12, may interact with a user interface of external programmer 20 to program stimulator 14 or retrieve from AIMD 14 information regarding operation of stimulator 14. Programming of AIMD 14 may refer generally to the generation and transfer of commands, programs, or other information to control the operation of the AIMD 14. For example, programmer 20 may transmit programs, parameter adjustments, program selections, group selections, or other information to control the operation of AIMD 14, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

Programmer 20 may be a clinician programmer or a patient programmer. An example of a commercially available clinician programmer is the Medtronic N'Vision® Programmer Model 8840, marketed by Medtronic, Inc., of Minneapolis, Minn. An example of a commercially available patient programmer is the Medtronic myStim® Programmer, marketed by Medtronic, Inc. In some cases, external programmer 20 may be a physician or clinician programmer if it is primarily intended for use by a physician or clinician. In other cases, external programmer 20 may be a patient programmer if it is primarily intended for use by a patient. In general, a physician or clinician programmer may support selection and generation of programs or parameters by a clinician for use by AIMD 14. A clinician programmer may permit a clinician to control or adjust a larger set of therapy parameters than a patient programmer allows a patient to adjust. For example, a clinician programmer may allow a clinician to define new therapy programs or therapy parameter sets, or to modify parameters of an existing therapy program within a wide range, e.g., a parameter range accessible by hardware and/or software AIMD 14. In contrast, a patient programmer may only allow a patient to select among predetermined therapy programs or to modify one or more therapy parameters within a range defined by the physician and programmed in the patient programmer. In some examples, a patient programmer may be configured to be portable and carried by patient 12 during a daily routine. In some examples, a medical device system 10 may include both a patient programmer and a clinician programmer, which may enable a clinician to program AIMD 14 and/or the patient programmer and may allow patient 12 some control over his or her therapy.

AIMD 14 may be implanted in patient 12 at a location minimally noticeable to the patient. Alternatively, stimulator may be external to patient 12 and coupled to implanted leads via a percutaneous extension. For spinal cord stimulation (SCS), as an example, AIMD 14 may be located, among other locations, in the lower abdomen, lower back, or other location to secure the stimulator. Leads 16 may be tunneled from AIMD 14 through tissue to reach the target tissue adjacent to spinal cord 18 for stimulation delivery. At distal portions of leads 16 are one or more electrodes (not shown) that transfer stimulation energy from the lead to the tissue. The electrodes may be electrode pads on a paddle lead, circular (i.e., ring) electrodes, surrounding the body of leads 16, segmented electrodes arranged at different axial and rotational positions around a lead, conformable electrodes, cuff electrodes, or any other type of electrodes capable of forming unipolar, bipolar or multipolar electrode configurations. In general, segmented electrodes arranged at selected axial and rotational positions at the distal ends of leads 16 will be described for purposes of illustration.

In the example of FIG. 1, each of the electrode combinations specifies a combination of electrodes arranged along lengths of two or more leads. If each lead 16 includes four ring electrodes, then the leads can be viewed as having four axial positions or levels. For segmented electrodes, an electrode may occupy a rotational arc at a given axial position of the lead. In some cases, the rotational arc may be similar to a portion of a ring electrode. For example, instead of a ring electrode that extends 360 degrees around a lead body, three, separate ninety degree segments could be provided to form three segmented electrodes at a given axial position along the length of the lead. Hence, two or more segmented electrodes may be provided at the same axial position but at different, non-overlapping rotational positions. Alternatively, a single segmented electrode could be provided at each of multiple axial levels. In general, in each case, a segmented electrode or electrode segment may have a dimension that spans only a portion of the circumference of the lead, unlike a ring electrode which generally extends around the entire circumference.

An electrode combination may include combinations of electrodes on the same lead or multiple leads, as well as one or more electrodes on a housing of AIMD 14 in some cases. In each case, some electrodes in an electrode combination may form anodes while other electrodes form cathodes, establishing paths for flow of electrical stimulation current relative to an anatomical target such as spinal cord nerve tissue at a desired position on the spinal cord. As an example, for SCS, stimulation may be delivered in the vicinity of the T7, T8 and T9 vertebrae, although other positions on the spinal cord are possible. In a current-based system, electrodes may be selected to form anodes or cathodes coupled to regulated current sources and sinks, respectively.

Figure 2:
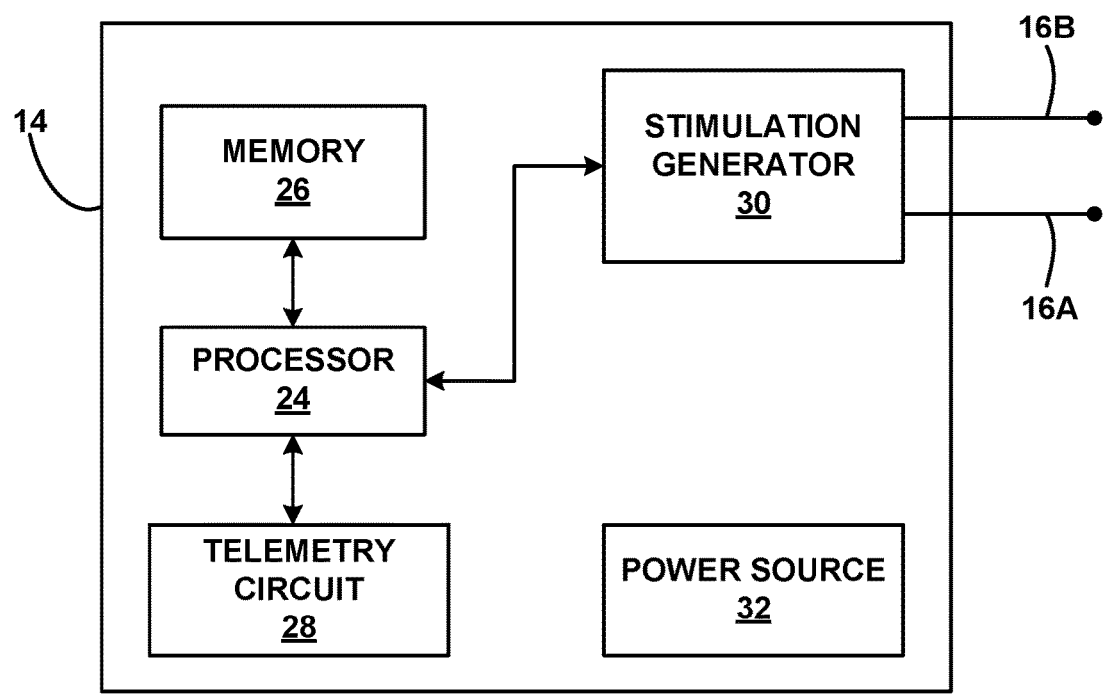
FIG. 2 is a functional block diagram illustrating various example components of an implantable electrical stimulation system.

FIG. 2 is a functional block diagram illustrating various components of an AIMD 14. In the example illustrated in FIG. 2, AIMD 14 includes a processor 24, memory 26, stimulation generator 30, telemetry circuit 28, and power source 32. Memory 26 may store instructions for execution by processor 24, stimulation therapy program data, sensor data, operational and status data, and any other electronic information regarding therapy or patient 12. Such information in memory 26 may assist in determining whether AIMD 14 is compatible with an MRI modality, as described in further detail below. Stimulation program data may include stimulation parameters transmitted from programmer 20, as well as programs defined by such parameters, and program groups. Some data may be recorded for long-term storage and retrieval by a user. Memory 26 may include separate memories for storing different types of data.

In some examples, memory 26 also may store information pertinent to compatibility of AIMD 14 with an MRI modality. For example, memory 26 may store a date on which AIMD 14 and/or leads 16 were implanted in patient 12, a date on which any revision was made to AIMD 14 and/or leads 16, a presence of another IMD implanted in patient 12, or a name and/or phone number of a physician who implanted AIMD 14 or manages care of patient 12. In some examples, memory 26 may store a manufacturer of AIMD 14 and contact information for the manufacturer, an identifier of AIMD 14 and/or leads 16, such as a serial number, model number, registration number, name, or the like, and/or a magnetic field magnitude to which AIMD 14 can be exposed. Additionally or alternatively, memory 26 may store information regarding an implant location of AIMD 14 and/or leads 16, an indication of the presence of an abandoned, broken, or damaged lead 16, or an impedance of one or more of leads 16 (and, if present, lead extensions or adaptors).

Processor 24 controls stimulation generator 30 to deliver electrical stimulation via electrode combinations formed by electrodes in one or more electrode arrays. For example, stimulation generator 30 may deliver electrical stimulation therapy via electrodes of one or more leads 16, e.g., as stimulation pulses or continuous waveforms. Stimulation generator 30 may include stimulation generation circuitry to generate stimulation pulses or waveforms and switching circuitry to switch the stimulation across different electrode combinations, e.g., in response to control by processor 24. In particular, processor 24 may control the switching circuitry on a selective basis to cause stimulation generator 30 to deliver electrical stimulation to selected electrode combinations and to shift the electrical stimulation to different electrode combinations. Alternatively, in some embodiments, stimulation generator 30 may include multiple current or voltage sources to control delivery of stimulation energy to selected combinations of electrodes carried by leads 16.

Electrode combinations and other parameters associated with different therapy programs may be represented by data stored in a memory location, e.g., in memory 26, of AIMD 14. Processor 24 may access the memory location to determine the electrode combination for a particular program and control stimulation generator 30 to deliver electrical stimulation via the indicated electrode combination. Each program may specify a set of parameters for delivery of electrical stimulation therapy. As an example, a program may specify electrode combination, electrode polarities, current or voltage amplitude, pulse rate and pulse width. Additional parameters such as duty cycle, duration, and delivery schedule also may be specified by a therapy program.

Using an external programmer, such as programmer 20, a user may select individual programs for delivery on an individual basis, or combinations of programs for delivery on a simultaneous or interleaved basis. In addition, a user may adjust parameters associated with the programs. The programs may be stored in memory 26 of AIMD 14. Alternatively, the programs may be stored in memory associated with external programmer 20. In either case, the programs may be selectable and adjustable to permit modification of therapy parameters. In some examples, programmer 20 may be a patient programmer, which may allow patient 12 to select among programs programmed by a clinician and stored in a memory of AIMD 14 or the patient programmer. Additionally or alternatively, a patient programmer may allow patient 12 to adjust therapy parameters within a range determined by a clinician and stored in memory of the patient programmer or AIMD 14. In addition, a physician programmer may permit generation of new programs, which may be loaded into memory 26, and adjustment of parameters associated with existing programs.

Upon selection of a particular program or program group from memory 26, processor 24 may control stimulation generator 30 to deliver stimulation according to the programs in the groups, e.g., simultaneously or on a time-interleaved basis. A group may include a single program or multiple programs, each of which specifies an electrode combination. Again, the electrode combination may specify particular electrodes in a single array or multiple arrays, e.g., on a single lead or among multiple leads.

AIMD 14 may be responsive to adjustments of programming parameters and electrode configurations by a user via programmer 20. In particular, processor 24 may receive adjustments to program parameters from programmer 20 via telemetry circuit 28. Telemetry circuit 28 may support wireless telemetry with external programmer 20 or another device by radio frequency (RF) communication, proximal inductive interaction of AIMD 14 with external programmer 20, or other techniques. Telemetry circuit 28 may send information to and receive information from external programmer 20 on a continuous basis, at periodic intervals, or upon request from the stimulator or programmer. To support RF communication, telemetry circuit 28 may include appropriate electronic components, such as amplifiers, filters, mixers, encoders, decoders, modulators, demodulators and the like. In some examples, processor 24 also may communicate information to programmer 20 or another external device via telemetry circuit 28.

In some examples, memory 26 also may store parameters of different operating modes of AIMD 14. For example, one operating mode may be an MRI conditionally safe operating mode. In some examples, when in an MRI conditionally safe operating mode, processor 24 may suspend therapy delivery and enter a low power state. Processor 24 may switch from a normal operating mode, in which stimulation generator 30 delivers therapy to patient 12 via electrodes carried by leads 16, to an MRI conditionally safe operating mode in response to an instruction received from an external device, such as, for example, programmer 20. In some examples, in the MRI conditionally safe operating mode, processor 24 may control the components of AIMD 14 to be in a low power mode that provides sufficient functionality to the components, e.g., processor 24 and stimulation generator 30, to prevent stimulation therapy from accidentally being delivered to patient 12 during the MRI. In the MRI conditionally safe operating mode, according to some examples, AIMD 14 may remain awake (operational) but does not actively deliver electrical stimulation to the patient.

Power source 32 delivers operating power to the components of stimulator 14. Power source 32 may include a small rechargeable or non-rechargeable battery and a power generation circuit to produce the operating power. Recharging may be accomplished through proximal inductive interaction between an external charger and an inductive charging coil within AIMD 14. In some embodiments, power requirements may be small enough to allow AIMD 14 to utilize patient motion and implement a kinetic energy-scavenging device to trickle charge a rechargeable battery. In other embodiments, traditional non-rechargeable batteries may be used for a limited period of time. As a further alternative, an external inductive power supply could transcutaneously power AIMD 14 when needed or desired.

Figure 3:
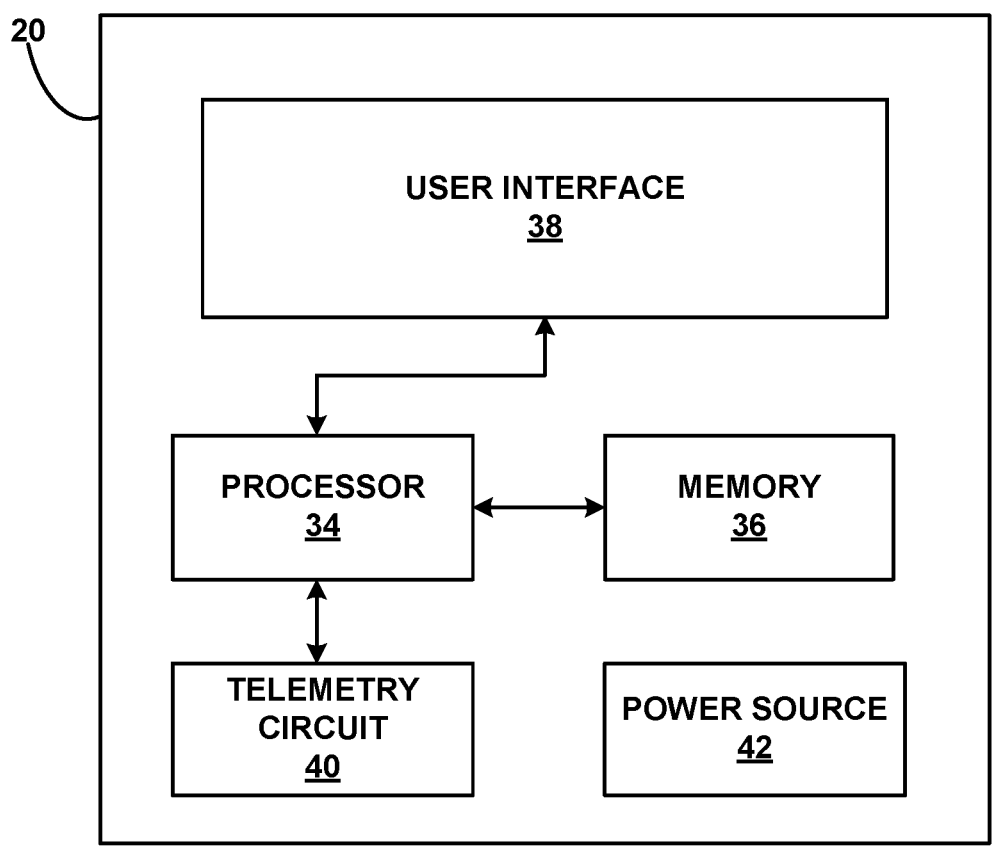
FIG. 3 is a functional block diagram illustrating various example components of an external programmer, such as a patient programmer or clinician programmer, for use in programming parameters and retrieving information from an active implantable medical device.

FIG. 3 is a functional block diagram illustrating various components of an external programmer 20 for an AIMD 14. As shown in FIG. 3, external programmer 20 includes processor 34, memory 36, telemetry circuit 40, user interface 38, and power source 42. In some examples, external programmer 20 may be a patient programmer. A patient programmer may be portable and may be carried by patient 12 throughout his or her daily routine. A patient programmer may allow a patient to interact with user interface 38 to select programs, adjust program parameters, and retrieve information from AIMD 14, e.g., on a limited basis as specified by the clinician. For example, the patient programmer may be configured to permit the patient amplitude, pulse width, or pulse rate adjustments to be made only within a limited range, or to permit only particular sets of electrode configurations to be selected by the patient. In examples in which external programmer 20 is a patient programmer, the patient programmer may allow the patient or another user, such as an MRI technician or radiologist, to determine whether AIMD 14 is compatible with an MRI modality. Additionally, in some examples, the patient programmer may allow the patient or other user to instruct the AIMD 14 to enter an MRI conditionally safe operating mode, which may configure the AIMD 14 in a mode compatible with a scan by an MRI modality.

By utilizing a patient programmer to determine whether AIMD 14 is compatible with an MRI modality, the patient may not need to visit a physician who is managing therapy provided by AIMD 14 in order to determine whether AIMD 14 is compatible with the MRI modality or to modify the operating mode of AIMD 14 to the MRI conditionally safe operating mode. In this way, the patient programmer may facilitate and expedite determination of whether AIMD 14 is compatible with an MRI modality and preparation of AIMD 14 for the scan by the MRI modality. In some examples, the patient programmer may implement at least one technique to enable patient 12 or another user to utilize the patient programmer to make the MRI compatibility determination without error or complication, as will be described below. For example, the patient programmer may automatically gather the information used to make the MRI compatibility determination and make the determination automatically without intervention by patient 12 or another user.

In other examples, external programmer 20 may be a clinician programmer. In the case of a clinician programmer, a clinician interacts with user interface 38 in order to generate programs, adjust program parameters, such as voltage or current amplitude, pulse width, pulse rate, electrode combinations and electrode polarities. A clinician programmer may permit a clinician to control or adjust a larger, and perhaps complete, set of therapy parameters, relative to the limited set of parameters adjustable via a patient programmer. The clinician may also interact with user interface 38 in order to retrieve information from AIMD 14, such as information pertinent to compatibility of AIMD 14 with an MRI modality, e.g., stored in memory 26 of AIMD 14. Generation of programs and adjustment of program parameters may be aided by automated programming algorithms that guide the physician or clinician to select particular programs and program parameters.

User interface 38 may include a screen and one or more input buttons that allow external programmer 20 to receive input from a user. The screen may be a liquid crystal display (LCD), touch screen, or the like. The input buttons may include a touch pad, increase and decrease buttons, emergency shut off button, and other buttons needed to control the stimulation therapy. In some cases, the user may interact with user interface 38 via a stylus, soft keys, hard keys, directional devices, and any of a variety of other input media. Processor 34 receives input from user interface 38, presents data via the user interface, retrieves data from memory 36 and stores data within memory 36. Processor 34 also controls the transmission of data via telemetry circuit 40 to AIMD 14. Memory 36 may include operational instructions for processor 34 or program parameter sets. For example, memory 36 may be a computer readable storage medium comprising instructions that cause processor 34 to perform various functions.

In some examples, memory 36 also may store information pertinent to compatibility of AIMD 14 with an MRI modality. For example, memory 36 may store a date on which AIMD 14 and/or leads 16 were implanted in patient 12, a date on which any revision was made to AIMD 14 and/or leads 16, or a name and/or phone number of a physician who implanted AIMD 14 or manages care of patient 12. In some examples, memory 36 may store a manufacturer of AIMD 14 and contact information for the manufacturer, an identifier of AIMD 14 and/or leads 16, such as a serial number, a model number, a registration number, or the like, or a magnetic field magnitude to which AIMD 14 safely can be exposed without harm to patient 12. Additionally or alternatively, memory 36 may store information regarding an implant location of AIMD 14 and/or leads 16, a presence of another IMD implanted in patient 12, an indication of the presence of an abandoned, broken, or damaged lead 16, or an impedance of one or more of leads 16.

Telemetry circuit 40 allows the transfer of data to and from AIMD 14. Telemetry circuit 40 may communicate automatically with telemetry circuit 28 of AIMD 14 at a scheduled time or when the telemetry circuit detects the proximity of the stimulator. Alternatively, telemetry circuit 40 may communicate with AIMD 14 when signaled by a user through user interface 38. To support RF communication, telemetry circuit 40 may include appropriate electronic components, such as amplifiers, filters, mixers, encoders, decoders, modulators, demodulators and the like.

In some examples, telemetry circuit 40 may be used to obtain information from memory 26 of AIMD 14 that is pertinent to compatibility of AIMD 14 with an MRI modality. For example, in response to an input from a user via user interface 28, such as an MRI compatibility input entered via user interface 38, processor 34 may transmit an instruction via telemetry circuit 40 to processor 24 of AIMD 14 to retrieve MRI compatibility information from memory 26 and transmit the MRI compatibility information via telemetry circuit 28 to external programmer 20. Processor 34 then may utilize the MRI compatibility information to determine whether AIMD 14 is compatible with an MRI modality. In some examples, processor 34 may display the results of the determination, e.g., that AIMD 14 is MRI compatible or MRI incompatible, to a user, such as patient 12, via user interface 38. Such a technique may be carried out by an external programmer 20 comprising either a clinician programmer or a patient programmer. A patient programmer that is able to obtain MRI compatibility information and utilize the information to make an MRI compatibility determination or transmit the MRI compatibility information to another device may facilitate determination of MRI compatibility between AIMD 14 and an MRI modality without visiting a clinician who is managing therapy provided by AIMD 14. In this way, the patient programmer may facilitate and expedite determination of whether AIMD 14 is compatible with an MRI modality and preparation of AIMD 14 for the scan by the MRI modality.

Based on the results of the determination, in some examples, the user may then input a command via user interface 38 to cause the AIMD 14 (e.g., processor 24 and stimulation generator 30) to enter an MRI conditionally safe operating mode. Processor 34 may transmit the command to processor 24 of AIMD 14 via telemetry circuits 40, 28. In other examples, when processor 34 determines that AIMD 14 is compatible with the MRI modality, processor 34 may automatically generate and transmit to processor 24 of AIMD 14 a command that causes AIMD 14 (e.g., processor 24 and stimulation generator 30) to enter an MRI conditionally safe operating mode. In additional examples, e.g., in which AIMD 14 is MRI safe or MRI conditionally safe without entering an MRI conditionally safe operating mode, the patient may simply proceed with the MRI procedure, based on the verification of MRI compatibility, with or without configuring AIMD 14 to enter an MRI conditionally safe operating mode.

Power source 42 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 4:
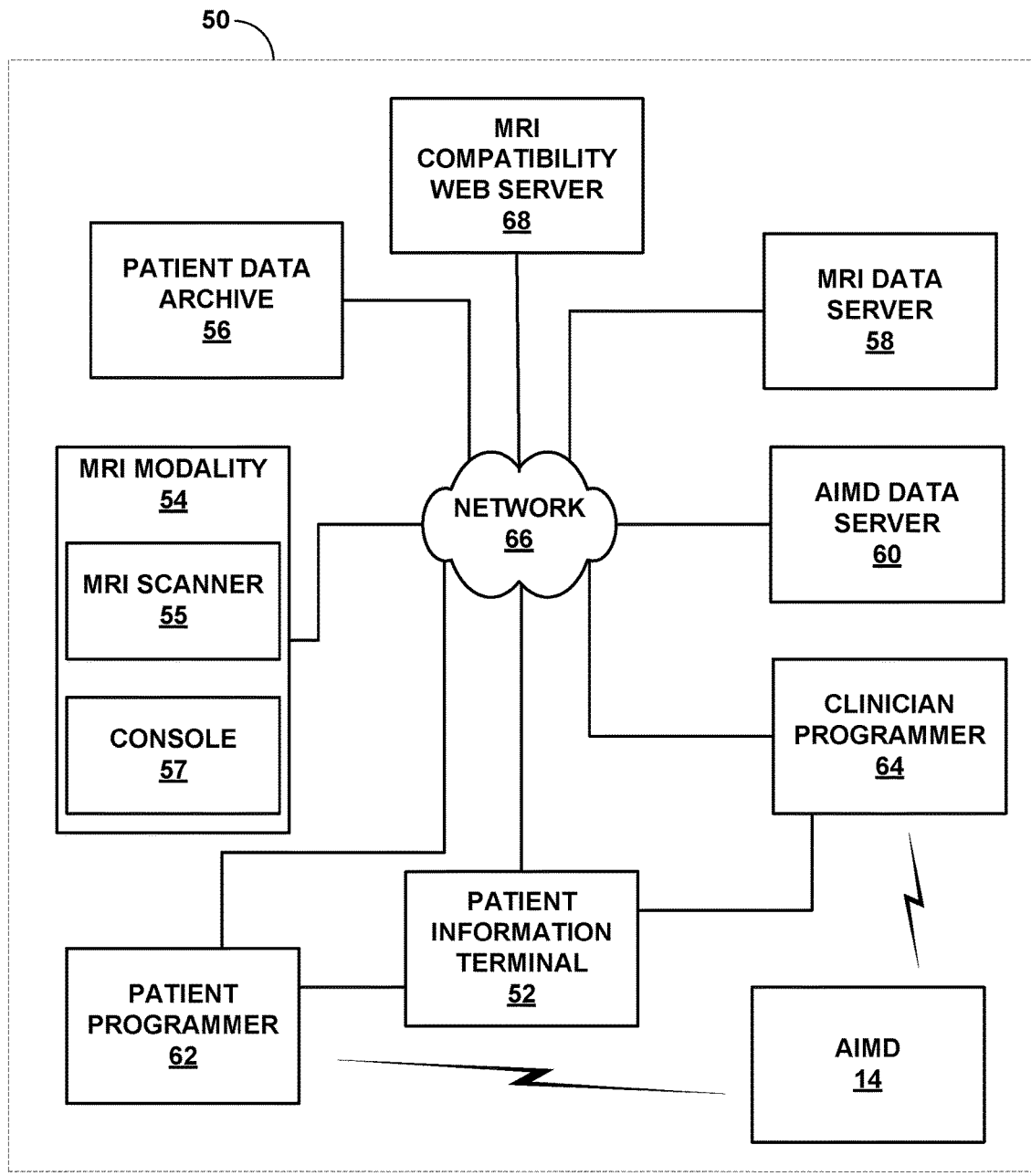
FIG. 4 is a functional block diagram illustrating a system that may be used to determine compatibility of an AIMD and an MRI modality.

FIG. 4 is a conceptual diagram illustrating an example computing system 50 that includes a number of computing devices that may be connected to a network 66. In some examples, one or more of the devices of system 50 may perform the techniques described in this disclosure, or may facilitate performance of the techniques described in this disclosure by a user, such as, for example, a medical technician, clinician, or patient 12. In the example illustrated in FIG. 4, AIMD 14, patient programmer 62, clinician programmer 64, patient information terminal 52, MRI modality 54, patient data archive 56, MRI compatibility web server 68 MRI data server 58, and AIMD data server 60 are connected via a network 66. While FIG. 4 shows system 50 as including nine devices connected via network 66, in other examples system 50 may include fewer than eight devices or more than eight devices. For example, in some cases system 50 may include two or more of the devices depicted in FIG. 4.

In the example of FIG. 4, system 64 includes a network 66. Network 66 may be a wired or wireless network, or may comprise a combination of wired and wireless networks. In some cases, network 66 may be formed by a local area network, a wide area network, or a global network such as the Internet, or various combinations of such networks. As alternatives, one or more of the devices may exchange information with another device by other techniques, such as direct connect interfaces, infrared telemetry, wireless telemetry, exchange of data storage media such as memory cards or disks, or the like. The communication links between various devices illustrated in FIG. 4 may be accomplished through wired communication protocols, wireless communication protocols, or combinations thereof.

Patient information terminal 52 may include, for example, a laptop computer, a desktop computer, or a workstation located remote from the MRI facility executing a software program or accessing a website, into which the patient may enter and/or from which the patient may retrieve MRI compatibility information prior to arriving at the MRI facility. The website may be provided by MRI compatibility web server 68, which may be configured to serve web pages to guide MRI compatibility information collection, storage and retrieval to support the compatibility determination. In other examples, the patient information terminal may include a computer at the MRI facility that executes a software program or accesses a website into which the patient may enter and/or from which the patient may retrieve MRI compatibility information. In some cases, patient 12 may enter MRI compatibility information in patient information terminal 52, while in other cases a medical technician or clinician may collect MRI compatibility information from patient 12 and enter the information in the patient information terminal 52. In some examples, a staff member of the MRI facility may enter and/or retrieve some information during registration of the patient at a computing device associated with the MRI facility, e.g., based on information obtained from the patient over the telephone, or over other electronic communication media, such as email, web chat, video teleconference, or the like. Hence, the patient information terminal 52 may be located at the MRI facility or elsewhere, or presented by a web page or other computer interface at a location remote from the MRI facility.

In some examples, patient information terminal 52 may execute a software program or access a website, such as a website provided by MRI compatibility web server 68, which provides instructions regarding the MRI compatibility information to be obtained from patient 12. For example, patient information terminal 52 may execute an application program that executes locally on patient information terminal 52 or remotely via network 66 and prompts a user, such as a medical technician, clinician, or patient 12 to input pertinent MRI compatibility information. Again, the program may be executed locally, or may be accessed via the network. The program may prompt the user to enter MRI compatibility information, and in some examples, may be programmed to evaluate the MRI compatibility information entered by the user and present subsequent prompts to the user based on previously entered MRI compatibility information.

The user may input MRI compatibility information regarding the AIMD 14 and patient 12 in patient information terminal 52. For example, the user may input a date on which AIMD 14 and/or leads 16 were implanted in patient 12 or a date on which a revision was made to AIMD 14 and/or leads 16. The revision may include, for example, a subsequent surgical procedure to repair or modify AIMD 14 or a surgical procedure to replace, modify, or implant leads 16 that connect to AIMD 14. The user also may input a name and/or phone number of a physician who implanted AIMD 14 in patient 12. In some cases, the user may further input the name and/or phone number of a physician who manages the care of patient 12, including therapy delivered by AIMD 14. The user also may input the name of the manufacturer of AIMD 14, a website address of the manufacturer, or an identifier of AIMD 14 and/or leas 16, such as a model number, a serial number, a registration number, or the like. In some examples, the user may additionally or alternatively input that patient 12 has another IMD implanted in his or her body and, optionally, MRI compatibility information regarding the other IMD.

In some examples, the user also may input information regarding a location at which AIMD 14 is implanted in patient 12, such as, for example, torso, right or left leg, cranium, or more specific location information. The user may collect the implant location information from patient 12, may retrieve the implant location from memory 36 of programmer 20, or may retrieve the implant location from memory 26 AIMD 14 via programmer 20. In other examples, the user may determine the implant location using a metal detector or an x-ray imaging device which detects a radio-opaque marker in AIMD 14 and/or leads 16. In examples in which the AIMD 14 is compatible with an MRI modality, the user may further input a magnetic field strength with which AIMD 14 is compatible, e.g., based on retrieval of information indicating the threshold.

In some examples, at least some of the MRI compatibility information discussed above may be stored on a patient ID card or AIMD Compatibility Documentation. Patient 12 may carry the patient ID card as a reference for the information contained thereon, and may present the patient ID card to a user, who then enters the information from the patient ID card in patient information terminal 52. In other examples, patient 12 may enter the MRI compatibility information from the patient ID card in patient information terminal 52. The patient ID card may assist the user in obtaining pertinent MRI compatibility information in cases in which patient 12 is not able to communicate the pertinent information, e.g., because of language barriers, a medical condition such as loss of consciousness, or the like.

AIMD Compatibility Documentation may also contain at least some of the information discussed above. The AIMD Compatibility Documentation may have been produced recently by a health care provider, such as an implanting, managing, or referring physician, based on the health care provider's knowledge of the MRI compatibility of AIMD 14. AIMD Compatibility Documentation may be possessed by patient 12 and communicated or provided to a user who enters the pertinent data into patient information terminal 52 or another computing device. The MRI Compatibility Documentation may assist the user in obtaining pertinent MRI compatibility information in cases in which patient 12 is not able to communicate the pertinent information, e.g., because of language barriers, a medical condition such as loss of consciousness, or the like.

In some examples, at least some of the MRI compatibility information discussed above may be stored in memory 26 of AIMD 14. Information stored in memory 26 may be retrieved by via external programmer 20 or another device, e.g., via wireless telemetry, and may be communicated to another device via network 66. Memory 26 may store, for example, one or more of an implant date or a revision date, a physician name and/or telephone number, a manufacturer name, a serial number, a model number, a registration number, an implant location, a magnetic field strength, a presence of another IMD implanted in patient 12, or the like. In some examples, some MRI compatibility information may be stored in memory 26 of AIMD 14 while some MRI compatibility information is stored in memory 36 of external programmer 20. In some examples, at least some of the MRI compatibility information may be stored in memory 26 and memory 36. External programmer 20 then may communicate the MRI compatibility information to another device, such as, for example, MRI modality 54 or patient information terminal 52, via network 66.

In some examples, at least some of the MRI compatibility information discussed above may be stored in memory 36 of patient programmer 62. Patient programmer 62 may include components similar to those illustrated in FIG. 3 for external programmer 20 (e.g., processor 34, memory 36, user interface 38, telemetry circuit 40, and power source 42). In some examples, patient programmer 62 may connect to network 66 and may communicate the MRI compatibility information in response to a query from another device, such as, for example, MRI modality 54, patient information terminal 52, or the like. In other examples, a user, such as patient 12, may retrieve MRI compatibility information from memory 36 of patient programmer 62 via user interface 38. The MRI compatibility information stored on patient programmer 62 may include, for example, one or more of an implant date or a revision date, a physician name and/or telephone number, a manufacturer name, a serial number, a model number, a registration number, an implant location, a magnetic field strength with which AIMD 14 is compatible, a presence of another IMD implanted in patient 12, or the like.

Patient programmer 62 may allows a patient to interact with user interface 38 to select therapy programs, adjust therapy program parameters, and retrieve information from AIMD 14, e.g., on a limited basis as specified by the physician or clinician. Patient programmer 62 may be portable or highly portable and allow patient 12 to carry or utilize patient programmer 62 throughout their day. Patient programmer 62 may allow the patient or another user, such as an MRI technician or radiologist, to determine whether AIMD 14 is compatible with MRI modality 54. Additionally, in some examples, patient programmer 62 may allow the patient or other user to instruct the AIMD 14 to enter an MRI conditionally safe operating mode, which may configure the AIMD 14 in a mode compatible with a scan by MRI modality 54.

In some examples, a user, such as a clinician or MRI technician, may utilize clinician programmer 64 to retrieve MRI compatibility information stored in memory 36 of patient programmer 62 or memory 26 of AIMD 14. A clinician programmer may permit a clinician to control or adjust a larger set of therapy parameters of AIMD 14 than a patient programmer, and may be utilized by the clinician who implanted AIMD 14 or manages therapy delivered to patient 12 by AIMD 14. Clinician programmer 64 may include components similar to those illustrated in FIG. 3 for external programmer 20 (e.g., processor 34, memory 36, user interface 38, telemetry circuit 40, and power source 42). The MRI compatibility information retrieved using clinician programmer 64 may include, for example, one or more of an implant date or a revision date, a physician name and/or telephone number, a manufacturer name, a serial number, a model number, a registration number, an implant location, a magnetic field strength with which AIMD 14 is compatible, a presence of another IMD implanted in patient 12, or the like.

Some of the MRI compatibility information may be stored in AIMD data server 60, which may be maintained by the manufacturer of AIMD 14, the hospital or clinic at which AIMD 14 was implanted in patient 12, or a third party. AIMD data server 60 may store any of the MRI compatibility information regarding AIMD 14, including, for example, implant date or revision date, physician name and/or telephone number, manufacturer name, serial number, a model number, a registration number, implant location, compatible magnetic field strength, or the like. In other cases, AIMD data server 60 may not store MRI compatibility information specific to the patient 12, but may store MRI compatibility information relating to design specifications or MRI compatibility of particular AIMD models. In some examples, at least some of the MRI compatibility information may be stored by at least two of AIMD data server 60, memory 26 of AIMD 14, and memory 36 of patient programmer 62 or clinician programmer 64. AIMD data server 60 may communicate the MRI compatibility information via network 66 to another device connected to network 66.

Similarly, MRI data server 58 may store MRI compatibility information related to operation of MRI modality 54. MRI data server 58 may be operated by, for example, the manufacturer of MRI modality 54, the hospital or clinic which operates imaging modality 54, or a third party. MRI data server 58 may store, for example, operational parameters of the particular MRI modality 54, or different types of MRI modalities, such as magnetic field magnitude, a RF coil type, e.g., single or multichannel, or the like. MRI data server 58 may communicate the information for the particular MRI modality 54 to be used for the imaging procedure to another device connected to network 66 upon receipt of a prompt to do so.

System 50 also includes a patient data archive 56. Patient data archive 56 may store information regarding the outcome of the techniques described in this disclosure. That is, patient data archive 56 may store answers to the questions investigated during practice of the described techniques. For example, patient data archive 56 may store each individual question and the answer to each question for each instance the technique is performed. Patient data archive 56 may associate the questions and answers with the particular patient 12 who was seeking clearance for an MRI scan. As another example, patient data archive 56 may store the outcome of the technique, e.g., MRI allowed or MRI not allowed, but may not store the answers to the individual questions of the technique. In some cases, the records maintained by patient data archive 56 may include a scope and form of information suitable for compliance with applicable regulatory requirements.

MRI modality 54 may include an MRI scanner 55 and an MRI console 57 that presents a user interface to a user that facilitates control of the MRI scanner 55. In some examples, the console 57 may allow a user, such as an MRI technician or a clinician to configure MRI scanner 55 to operate in a manner with which AIMD 14 is compatible. For example, the user may configure the MRI scanner 55 to produce a magnetic field having a magnitude compatible with AIMD 14. MRI scanner 55 may comprise a conventional MRI scanner, and may include, for example, a single channel or multiple channel RF coil.

Figure 5:
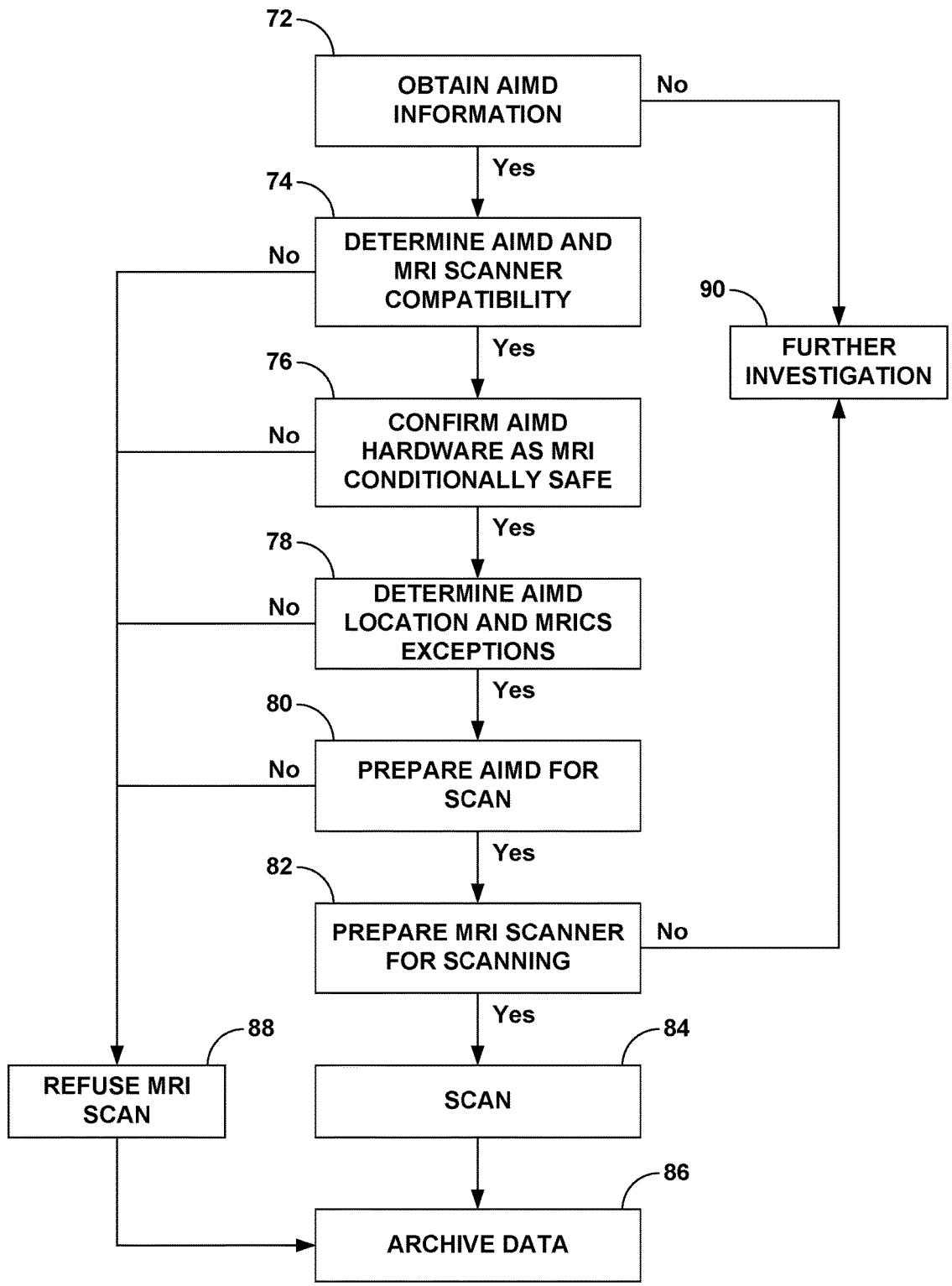
FIG. 5 is a flow diagram that depicts an example technique for determining compatibility of an active implantable medical device and an MRI modality.

FIG. 5 is a flow diagram illustrating one example technique according to which MRI compatibility of an AIMD 14 implanted in patient 12 may be determined. The example depicted in FIG. 5 includes six steps. However, in other examples, a technique for determining MRI compatibility of an AIMD 14 may not include all six steps. In general, a technique for determining MRI compatibility of AIMD 14 may include one or more of the steps depicted in FIG. 5.

For example, a technique for determining compatibility of AIMD 14 with an MRI modality, e.g., modality 54, may include three steps. The first step may include obtaining information regarding compatibility of AIMD 14 with an MRI scan. The second step may include obtaining MRI modality information regarding operation of an MRI modality. The third step may include determining whether AIMD 14 is compatible with the MRI modality based on the AIMD information and the MRI modality information.

The technique illustrated in FIG. 5 will be described as being performed by one or more of the computing devices of computing system 50 (FIG. 4) executing a software program or web pages. However, in other examples, the technique shown in FIG. 5 may be implemented at least in part using written materials such as a poster or instruction sheet and performed by a user. The poster or instruction sheet may guide a user, such as an MRI facility staff person, an MRI technician, a clinician, patient 12, or a combination of two or more of these users, in collecting and evaluating information regarding compatibility of AIMD 14 and MRI modality 54.

In the example shown in FIG. 5, one or more computing devices of system 50 first obtains AIMD information via one or more devices of system 50 (72). If an attempt to obtain AIMD information (72) is unsuccessful, as described below, further investigation (90) may be necessary, e.g., by an MRI technician or other person, to ensure MRI compatibility of the AIMD 14 implanted in the patient 12. As described above, one of a number of devices in system 50 may obtain the AIMD information. For example, system 50 may obtain AIMD information via entry by a user through patient information terminal 52 or MRI modality 54, or may obtain AIMD information from AIMD data server 60. In some examples, patient 12 may know and remember at least some of the AIMD information or may possess a patient ID card with the AIMD information printed thereon. Patient 12 may input the information when prompted by patient information terminal 52, which may be located at the MRI facility, in a clinic, or accessed remotely, or may provide the information to an MRI technician, clinician, or MRI facility staff person, e.g., orally or in writing, to enter the AIMD data into the appropriate device of system 50. In other examples, patient 12 may possess AIMD Compatibility Documentation produced by a health care provider such as an implanting, managing, or referring physician, which may provide at least some of the AIMD information. Patient 12 may input the information from AIMD Compatibility Documentation when prompted by patient information terminal 52, or may provide the information to an MRI technician, clinician, or MRI facility staff person to enter the AIMD data into the appropriate device of system 50. In still other examples, patient 12 may carry a patient programmer 62, and a memory 36 of patient programmer 62 may store at least some of the AIMD information. In some examples, instead of memory 36 of patient programmer 62 storing the AIMD information, a memory 26 of AIMD 14 may store at least some of the AIMD information and a user may utilize patient programmer 62 or a clinician programmer 64 to access the AIMD information. Patient programmer 62 or clinician programmer 64 may communicate the AIMD information to a patient information terminal 52 or network 66 upon prompting by terminal 52 or network 66.

As described above, the AIMD information may include, for example, an implant date of AIMD 14 and/or leads 16 in patient 12, a date at which a revision to AIMD 14 and/or leads 16 occurred, a presence of another IMD implanted in patient 12, a serial number, a model number, or a registration number of AIMD 14 and/or leads 16, the name or phone number of the physician who implanted the AIMD 14, the name or phone number of the physician managing care of patient 12, or a website or phone number of the manufacturer of AIMD 14. The AIMD information is used by a computing device of system 50 to determine features of AIMD 14 and whether AIMD 14 is compatible with an MRI modality 54 or an MRI scanner 55.

As described above with respect to FIG. 4, in some examples, patient information terminal 52 may comprise a web application or other computer program that patient 12 may access prior to or upon arriving at the MRI facility. In some cases, patient 12 may enter the AIMD information through patient information terminal 52 at his or her convenience prior to an MRI appointment. For example, patient 12 may access a website from a personal computer located at his or her home or another location. The web site may prompt patient 12 to enter AIMD information, and may guide patient 12 through entry of the AIMD information. For example, the website may include illustrations or other aids that assist patient 12 in retrieving the AIMD information from his or her patient ID card, a patient programmer, or AIMD 14 via the patient programmer. In some cases, a website may be presented by MRI compatibility web server 68 or by some other web server.

In other examples, a staff person at the MRI facility may contact patient 12 via a telephone call to collect the AIMD information prior to the arrival of patient 12 at the MRI facility. The staff person may contact patient 12 and enter the AIMD information into patient information terminal 52 or MRI modality 54 prior to scheduling the MRI procedure for patient 12, or may collect the AIMD information shortly before an appointment of patient 12, e.g., one to three days prior to the appointment.

In other examples, an MRI facility staff person may collect the AIMD information and input the AIMD information into patient information terminal 52 or MRI modality 54 when patient 12 registers for their appointment upon arrival at the MRI facility. In still other examples, an MRI technician or a clinician may collect the AIMD information and enter the AIMD information into patient information terminal 52 or MRI modality 54 during the appointment and prior to the MRI scan.

In some examples, the AIMD information may be stored in AIMD data server 60 (FIG. 4). AIMD data server 60 may be accessed by a user, such as patient 12, the staff person, the MRI technician, or the clinician to retrieve the AIMD information. In some cases, a processor, e.g., a processor of patient information terminal 52 or MRI modality 54, which is executing the software program or website, may access the information stored by AIMD data server 60 in response to instructions from the software program or website. Alternatively, MRI compatibility web server 68 may access AIMD data server 60 or MRI data server 58 automatically to obtain information for presentation or processing by MRI compatibility web server 68, patient information terminal 52, MRI modality 54, or other components. The instructions may be generated in response to other data input by the user, such as the name of patient 12, the manufacturer of the AIMD, the clinic or hospital at which AIMD 14 was implanted in patient 12, or the like.

In any of the above examples, upon collection, the AIMD information may be stored in a database that is accessible by any authorized device connected to a network, e.g., network 66. This may facilitate entry of different portions of the pertinent information at different devices or locations, e.g., MRI modality 54, patient information terminal 53, AIMD data server 60, or by different users, e.g., patient 12, a staff person at the MRI facility, an MRI technician, or a clinician. In some examples, the AIMD information stored in the database may be accessible subsequent to the appointment for which the information is being collected. For example, the AIMD information stored in the database may be accessible for use during evaluation of future MRI scans. In other examples, the AIMD information may be entered on a medical chart that facilitates organization of information and performance of the techniques described in this disclosure.

In examples in which the pertinent AIMD information can be obtained by one or more computing devices of system 50, e.g., patient information terminal 52, patient programmer 62, MRI modality 54, clinician programmer 64, AIMD data server 60, MRI data server 58, or MRI compatibility web server 68, the technique proceeds to determining compatibility between AIMD 14 and MRI scanner 55 (74). However, when the AIMD information cannot be obtained, such as when patient 12 has forgotten his or her patient ID card or cannot communicate the information due to language barriers or medical conditions, e.g., unconsciousness, further investigation is necessary prior to authorizing or refusing the MRI scan (90).

Once the AIMD information has been collected (72), one or more device in system 50 determines compatibility of AIMD 14 and the MRI scanner 55 at the MRI facility (74). In some examples, AIMD 14 may be compatible with certain types of MRI scanners, but may not be compatible with other types of MRI scanners. To determine compatibility between AIMD 14 and the particular MRI scanner 55, system 50 acquires information regarding the MRI modality 54, such as the type of MRI scanner 55, the RF coil type, and the like. For example, MRI compatibility web server 68 may interact with MRI data server 58 or MRI modality 54 to obtain such information.

In some examples, the type of MRI scanner 55 may include the model number and manufacturer of the MRI scanner 55. In other examples, the type of MRI scanner 55 may include the magnet type and the magnetic field strength produced by the MRI scanner 55. For example, an AIMD 14 may be compatible with an MRI scanner 55 that produces a magnetic field having a magnitude of 1.5 T. In other examples, the magnetic field with which AIMD 14 is compatible may be different (e.g., greater than 1.5 T or less than 1.5 T). The RF coil type may include an indication whether the RF coil is a single channel or a multiple channel RF coil.

A computing device of system 50 or a user interacting with system 50 may retrieve the MRI modality information from, for example, the MRI modality 54 itself, such as software used to operate the MRI modality 54 or physical labeling of the modality 54. In other examples, the MRI modality information may be stored on MRI data server 58 (FIG. 4) and may be accessed by a user, such as a staff person at the MRI facility, an MRI technician, or a clinician, or by a device such as MRI compatibility web server 68. In other examples, a device, e.g., patient information terminal 52 or MRI modality 54, that is executing an application software program or website may access the information stored by MRI data server 58 in response to an instruction from the software program or website.

The instructions may be generated in response to other information input by the user, such as the model number or serial number of MRI modality 54, the manufacturer of the MRI modality 54, the name of the MRI facility, or the like. As described above, MRI data server 58 may be maintained by the MRI facility, a manufacturer of the MRI modality 54, a manufacturer of AIMD 14, or a third party. In some examples, the user, MRI compatibility web server 68, patient information terminal 52, or MRI modality 54 may access MRI data server 58 indirectly by, for example, calling the maintainer of the database or accessing the database through a website or other computing interfaces. Notably, the various information collection and determination tasks may be performed by one computing device or distributed among various computing devices in system 50.

One or more of the computing devices of system 50 may compare the MRI modality information and the AIMD information to determine whether AIMD 14 is compatible with the MRI scanner 55 at the MRI facility (74). In some examples, patient information terminal 52, MRI compatibility web server 68, patient programmer 62, clinician programmer 64, or MRI modality 54 may determine whether AIMD 14 and the MRI scanner 55 are compatible based on the MRI modality information and the AIMD information. Any of such computing devices may be programmed or otherwise configured to automatically compare AIMD information and MRI modality information to determine compatibility of the particular AIMD with the particular MRI modality. In other examples, a user, such as an MRI technician, clinician, or MRI facility staff member, may make the compatibility determination based on the MRI modality information and the AIMD information. In some examples, the user may be assisted in making the determination by a software program or website executed by one of the devices in system 50.

For example, the computing device (e.g., patient information terminal 52, MRI compatibility web server 68, patient programmer 62, clinician programmer 64, or MRI modality 54) or a user may compare a magnetic field with which AIMD 14 is compatible to a magnetic field, e.g., a magnetic field produced by a particular set of MRI scan parameters, produced by the MRI scanner 55. If the computing device or user determines that AIMD 14 is not compatible with the MRI scanner 55 at the MRI facility, the computing device or user of system 50 outputs an indication that AIMD is incompatible with the MRI scanner 55 and the MRI scan is refused (88). In some examples, the computing device or user may not determine that AIMD 14 is incompatible with the MRI scanner 55, because one or both of the AIMD information and the MRI modality information may be incomplete, unclear, or conflicting. In these cases, the computing device may alert the user of the questionable information, and may refuse to authorize MRI scan until the information is corrected or provided. In other examples, when the user determines that AIMD 14 is not compatible with the MRI scanner 55 at the MRI facility, the user alerts patient 12 that an MRI scan will not be performed on patient 12.

However, when a computing device of system 50 or the user determines that AIMD 14 is compatible with the MRI scanner 55, the computing device or user proceeds to confirm that hardware of AIMD 14 is MRICS or MRIS (76). The computing device or user of system 50 may confirm that the AIMD 14 comprises MRICS or MRIS hardware by collecting information including, for example, the implant date of AIMD 14 and/or leads 16, the model number, serial number or registration number of AIMD 14 and/or leads 16, or other information. In some examples, the implant date may be utilized as a sort of threshold qualification in determining whether the implant comprises MRICS hardware. For example, it may be known that an AIMD 14 or leads 16 implanted prior to a certain date would not have included MRICS or MRIS hardware.

The information used to confirm that AIMD 14 comprises MRICS or MRIS hardware may further include a serial number, model number, or registration number of AIMD 14 and/or leads 16 coupled to AIMD 14. In some examples, the serial number, registration number, or model number may be provided on the patient ID card, or may be stored in memory 36 of patient programmer 62 or clinician programmer 64. In other examples, the serial number, registration number, or model number may be stored in memory 26 of IMB 16 and may be retrieved using patient programmer 62 or clinician programmer 64. The serial number, registration number or model number of AIMD 14 and leads 16 may be used by a computing device of system 50 or the user to retrieve information regarding AIMD 14 or leads 16 from an AMD data server 60, a manufacturer's website, a third party website, or via a phone call to the AIMD manufacturer or a third party. In some examples, the computing device that is executing the software program or website may utilize the serial number, registration number, or model number to retrieve data regarding the AIMD from AIMD data server 60. In some examples, the computing device may execute an algorithm that identifies certain values or patterns of a model number, registration number, or a serial number as corresponding to an AIMD that does or does not comprise MRICS or MRIS hardware. For example, the computing device may utilize the first four characters of a model number, registration number, or serial number of AIMD 14 or leads 16 and compare these four characters to a database including entries comprising the first four characters of a plurality of AIMDs or leads. The computing device may then make a determination of MRI compatibility of the AIMD 14 based on the results of the comparison of the characters of the serial number, registration number, or model number with entries in the database.

The information used by a computing device of system 50 to confirm that AIMD 14 comprises MRICS or MRIS hardware also may include a software lockout check. In some examples, memory 26 or AIMD 14 may store a serial number of AIMD 14, a serial number of leads 16 coupled to AIMD 14, and an implant location of AIMD 14 and leads 16. Based on the serial numbers and the implant location, AIMD 14 may determine whether the system, e.g., AIMD 14 and leads 16 is MRICS or MRIS. The software lockout check, then, may comprise interrogating AIMD 14 with patient programmer 62 or clinician programmer 64 to retrieve an indication of whether the system is MRICS or MRIS.

In other examples, upon implant of AIMD 14 and leads 16, an implanting physician or another user may communicate the serial number of AIMD 14, serial number of leads 16, and the implant location to a manufacturer of AIMD 14 or a third party, such as a third party that maintains MRI compatibility information for various AIMDs. The manufacturer or third party may determine whether the system is MRICS or MRIS based on the serial numbers and the implant location. In some examples, the manufacturer or third party may issue a MRICS card that indicates that AIMD 14 and leads 16 do or do not form an MRICS or MRIS system to patient 12, may issue a patient ID card with an indication that AIMD 14 and leads 16 do or do not form an MRICS or MRIS system, or may store the MRICS information for the system in a database on a server, e.g., AIMD data server 60 or patient data archive 56. The software lockout check, then, may include obtaining this information from the MRICS card, the patient ID card, or the database. In some examples, a manufacturer of AIMD 14 may provide a blank MRICS card to the implanting physician, who may fill out the MRICS with, for example, a serial number of AIMD 14 and/or leads 16, and implant location of AIMD 14 and/or leads 16, or an indication of whether the system formed by AIMD 14 and leads 16 is MRICS or MRIS. In some examples, the information used by a computing device of system 50 to confirm that AIMD 14 comprises MRICS or MRIS hardware may include implant information such as lead location or the presence of abandoned leads. In some examples, the implant information may be stored in memory 26 of IMD 16 and may be retrieved by a user via patient programmer 62 or clinician programmer 64. In other examples, the implant information may be stored in memory 36 of patient programmer 62 or clinician programmer 64.

In some examples, the implant information may be obtained by a user, such as a clinician, MRI technician or MRI facility staff person using a metal detector scan of patient 12 or an x-ray or fluoroscopy image of patient 12. For example, the metal detector scan of patient 12 may indicate approximate locations of metal objects in patient 12, which may include leads 16 and AIMD 14. In some examples, AIMD 14 or leads 16 may include a radio-opaque marker that may be seen on an x-ray image or a fluoroscopic image. The x-ray image or fluoroscopic image may facilitate more precise location of leads 16 or AIMD 14. When a computing device of system 50 determines that AIMD 14 does not comprise MRICS hardware (76), system 50 generates a notification that AIMD 14 is not compatible with the MRI scanner 55 and patient 12 will not undergo an MRI scan (88).

When a computing device of system 50 determines that AIMD 14 does, in fact, comprise MRICS or MRIS hardware, the computing device proceeds to prompt a user to determine and input the AIMD location and any MRICS hardware exceptions (78), e.g., via patient information terminal 52, patient programmer 62, or clinician programmer 64. In some examples, the user may determine the AIMD location or MRICS hardware exceptions by x-ray images or fluoroscopic images. For example, the x-ray or fluoroscopic images may show an abandoned lead, i.e., a lead that is not coupled to an IMD, or a lead that is broken or damaged. In other examples, the user may determine the AIMD location or MRICS hardware exceptions by retrieving information stored in memory 26 of AIMD 14 or memory 36 of patient programmer 62 or clinician programmer 64. In still other examples, system 50 or the user may retrieve the information from AIMD data server 60, by a phone call to the manufacturer of AIMD 14, or by accessing a website of the manufacturer. In some examples, retrieving the information from the manufacturer may require the serial number of AIMD 14, and may only work when AIMD 14 has been registered with the manufacturer.

Some locations at which AIMD 14 or leads 16 are implanted may preclude patient 12 from having an MRI scan. For example, leads 16 may be implanted proximate to a particular anatomical target of the patient 12, or near a target that does not correspond to a customary implant location. Similarly, leads 16 that are orphaned, i.e., unconnected to a stimulator, or damaged may preclude patient 12 from having an MRI scan due to potential overheating of the leads 16. When a computing device of system 50 determines that AIMD 14 is implanted in a location that precludes an MRI scan or patient 12 has implanted leads 16 that are damaged or orphaned (78), the computing device may generate a notification to a user that patient 12 cannot undergo an MRI scan (88).

When a computing device of system 50 determines that the AIMD 14 is implanted in a location that does not preclude an MRI scan and patient 12 does not have any implanted leads that are damaged or orphaned, the computing device proceeds to prompt the user to prepare AIMD 14 for an MRI scan (80). In some examples, the user may prepare AIMD 14 for the MRI scan by controlling AIMD 14 to perform a lead impedance test for each lead 16A, 16B that is coupled to AIMD 14. The impedance test may be an open/close test that indicates whether any of leads 16 includes a broken conductor, which may produce an open circuit. The impedance test also may indicate presence of contact between two conductors, which results in a short circuit. In some examples, when the impedance test indicates an open circuit or a short circuit, the user may input this into a computing device in system 50 (e.g., patient information terminal 52, MRI modality 54, patient programmer 62, or clinician programmer 64). A computing device of system 50 may then generate a notification to the user that patient 12 cannot undergo an MRI scan (88). In other examples, when the impedance test indicates an open circuit or a short circuit the user may recognize that this prevents patient 12 from undergoing an MRI scan, and the user may notify patient 12 of this fact (88).

However, when the impedance test indicates that the leads 16 are functional and AIMD 14 is functioning correctly, the user may proceed to ensure that AIMD 14 is in an MRI conditionally safe operating mode. In some examples, AIMD 14 may permanently be in an MRI conditionally safe operating mode (e.g., AIMD 14 is MRIS, or a normal operating mode of AIMD 14 is MRICS), and the user may not adjust AIMD 14 in any way. In other examples, the user may configure AIMD 14 to be in an MRI conditionally safe operating mode using external programmer 20. The MRI conditionally safe mode may include features that prevent AIMD 14 from inadvertently delivering stimulation to patient 12 during the MRI scan. For example, the MRI conditionally safe operating mode may place AIMD 14 in a low power state in which AIMD 14 does not deliver stimulation, but which prevents accidental provision of stimulation to patient 12. In some examples, AIMD 14 may include two or more MRI conditionally safe operating modes, which include different operating parameters, or which may result in AIMD 14 being compatible with different MRI scan parameters or different MRI modalities. In some examples, AIMD 14 may be providing life-sustaining therapy, and may not be able to be placed in an MRI conditionally safe operating mode in which stimulation is interrupted. In these examples, patient programmer 62 or clinician programmer 64 may indicate this fact to the user, and the user may inform patient 12 that he or she cannot undergo an MRI scan (88).

When AIMD 14 has been prepared for the MRI scan (80), a computing device of system 50 prompts the user to prepare the MRI scanner 55 for scanning (82). Preparation of the MRI scanner 55 for scanning includes, for example, scan parameter validation, e.g., setting or confirming MRI scan parameters according to which the MRI scanner 55 will scan patient 12. The MRI scan parameters may include, for example, a magnetic field magnitude and a gradient strength. A magnetic field that is too high may not be suitable for a patient 12 having an AIMD 14 implanted in his or her body, as described above. Similarly, a gradient strength that is too large may not be suitable for a patient having an AIMD 14 implanted in his or her body.

A user, such as a clinician or MRI technician, may be responsible for setting and confirming the MRI scan parameters. The user should confirm that the MRI scan parameters adhere to the guidelines of the AIMD 14 implanted in patient 12. In some examples, the user may consult a radiologist or a manufacturer of AIMD 14 for assistance in setting the MRI scan parameters. For example, the user may contact the manufacturer of AIMD 14 via a phone call or a website of the manufacturer.

The user may also confirm that the RF coil of the MRI scanner 55 is compatible with AIMD 14. For example, AIMD 14 may be compatible only with an MRI scanner 55 that include a single channel RF coil, and may not be compatible with an MRI scanner 55 that includes a multiple channel RF coil. As another example, a quadrature bird cage RF coil may function in linear mode and cause AIMD 14 to be exposed to an excessive magnetic field.

In some examples, the user may perform a test MRI scan, e.g., an MRI scan that is not performed on patient 12, to ensure proper functioning of the MRI RF coil. If the test scan fails to produce expected image quality or indicates improper operation of the MRI RF coil, the MRI scanner 55 may not be suitable to scan patient 12, and further investigation may be required (90).

In some examples, the MRI scanner 55 may include an AIMD mode that assures stringent internal limits on operation of the MRI scanner 55 to prevent AIMD 14 from being exposed to excessive magnetic fields. The user may configure the MRI scanner 55 in the AIMD mode prior to scanning patient 12. Once the MRI scanner 55 is prepared for scanning (82), the user may initiate the MRI scan of patient 12 (84).

Finally, regardless of whether the previous steps of the technique resulted in an MRI scan of patient 12 or a notification that patient 12 cannot undergo an MRI scan, the MRI compatibility information collected in the preceding steps and/or the results of the determinations made by a computing device of system 50 or a user may optionally be archived in patient data archive 56 (86). The archiving of the MRI compatibility information collected by the technique may provide defense against malpractice claims in the event patient 12 undergoes an MRI scan and is injured, or may provide evidence of regulatory compliance. As described above, patient data archive 56 may comprise database of MRI compatibility information regarding a plurality of patients, which may be maintained by the MRI facility, an organization with which the MRI facility is associated, or a third party. In some examples, patient data archive 56 may include an electronic and/or printed copy of the information collected and the determinations made by a computing device of system 50 or a user.

In some examples, some or all of the information collected in the various steps of the technique illustrated in FIG. 5 may be stored in a Digital Imaging and Communications in Medicine (DICOM) Modality Worklist record, which may be subsequently available to MRI technicians or other clinician. For example, AIMD information obtained in step (72) and MRI modality information obtained in step (74) may be stored in the DICOM Modality Worklist record. In some examples, this may enable the MRI scanner 55 to automatically configure itself in an AIMD mode upon identification of patient 12. Further, in some examples, the AIMD information may be saved into the DICOM images for future reference.

As described briefly above, although the above example may be directed to a technique implemented in software or a website by one or more computing devices in system 50, in other examples, the technique may be embodied in operations carried out by a user with the aid of written materials such as a poster or instruction sheet that guides a user to perform the steps of the technique described with reference to FIG. 5. The written materials may be presented in hard copy form or in soft copy form via a computer. The written materials may include graphical and/or textual information or instructions that facilitate determination of whether AIMD 14 and the MRI modality 54 satisfy the various determinations required to indicate compatibility between AIMD 14 and the MRI modality 54. Hence, the written materials may be presented to a user by a computing device as an interactive guide document for collecting information to determine compatibility of an AIMD and an MRI scanner. The computing device may then collect the information in the guide document upon entry by the user for use in the compatibility determination. In addition, such written materials may include areas to enter information, either electronically via a computer or manually via a writing instrument, to record collected information relating to the compatibility determination, as well as the compatibility determination itself.

Figure 6:
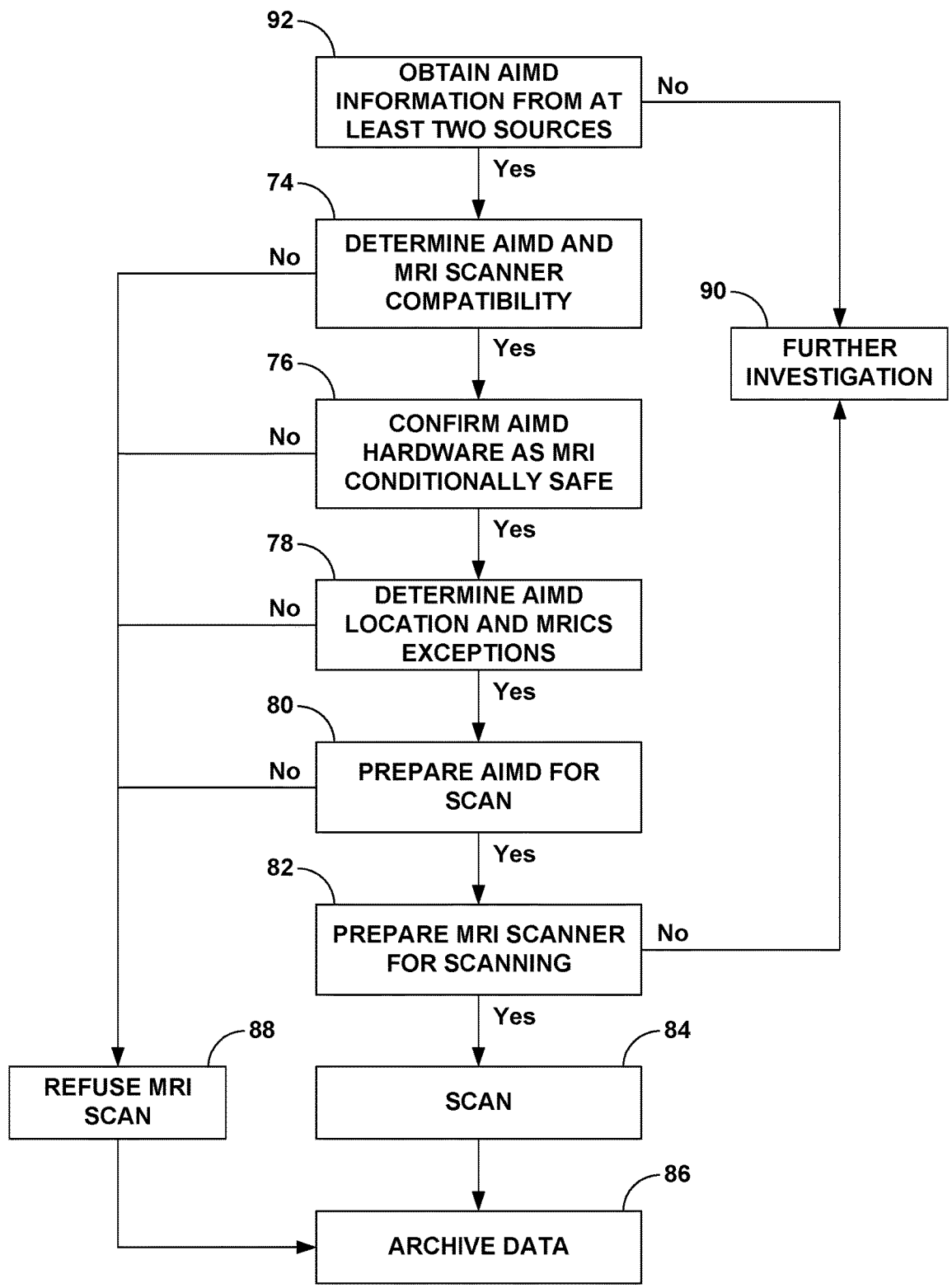
FIG. 6 is a flow diagram illustrating another example of a technique for determining compatibility of an AIMD and an MRI modality.

While the example illustrated in FIG. 5 is directed to one or more of the devices in system 50 obtaining the MRI compatibility information and determining or guiding a user in determining whether AIMD 14 is MRI compatible, in some examples, a technique which is automated may be implemented by a processor in a device of system 50. FIG. 6 is a flow diagram illustrating another example of a technique that may be performed to determine whether an AIMD 14 is compatible with an MRI modality 54. FIG. 6 will be described with concurrent reference to FIG. 4 for convenience, although the technique illustrated in FIG. 6 may be performed by another system, by a system comprised of a subset of the devices illustrated in FIG. 4, or the like.

The technique illustrated in FIG. 6 may be implemented by a processor. The processor may be included in one of the devices shown in FIG. 4. For example, one or more of patient information terminal 52, MRI modality 54, patient programmer 62, clinician programmer 64 or MRI compatibility web server 68 may form a computer hardware device that includes the processor. While described as being implemented by a processor, the technique shown in FIG. 6 may be implemented in hardware, software, firmware or any combination thereof. Additionally, the term processor is used to refer to one or more microprocessors, digital signal processors (DSPs), application specific integrated circuits (ASICs), field programmable gate arrays (FPGAs), or any other equivalent integrated or discrete logic circuitry, as well as any combinations of such components.

Initially, the processor may automatically obtain MRI compatibility information from at least two sources (92). As used herein, the phrase "automatically obtain MRI compatibility information" is used to denote a technique implemented by the processor which does not require user intervention once the technique has begun. In some examples, the automatic information retrieval may be initiated by a command from a user, such as patient 12, a MRI technician, a clinician, or the like. Once the technique is initiated, the processor may retrieve the MRI compatibility information from at least two sources without further intervention by the user.

The processor may automatically obtain MRI compatibility information from, for example, two or more of AIMD 14, patient programmer 62, clinician programmer 64, AIMD data server 60, MRI data server 58, patient data archive 56, and/or MRI modality 54. In some examples, the processor may be included in one of the devices (e.g., processor 34 of external programmer 20) and the processor may obtain at least some of the MRI compatibility information from a memory or database of the device in which the processor is located. Additionally or alternatively, the processor may utilize network 66 or another communication means to obtain the MRI compatibility information from at least one device in which the processor is not located. In some examples, the processor may obtain MRI compatibility information from at least two sources that are external to the device in which the processor is located.

As described above, the MRI compatibility information may include information regarding AIMD 14, leads 16, and/or MRI modality 54. For example, the MRI compatibility information may include a date on which AIMD 14 was implanted in patient 12, a date on which any revision was made to AIMD 14, an implant location of AIMD 14, or a name and/or contact information of a physician who implanted AIMD 14 or manages care of patient 12. In some examples, the MRI compatibility information may also include a serial number, registration number, or model number of AIMD 14 or contact information for the manufacturer of AIMD 14.

The MRI compatibility information may additionally, or alternatively, include information regarding leads 16 (and optionally, if present, lead extensions or adapters), such as, for example, a date on which leads 16 were implanted in patient 12, a date on which any revision was made to leads 16, an implant location of leads 16, an indication of the presence of an abandoned, broken or damaged lead 16, a serial number, registration number, or model number of leads 16, or an impedance of at least one of leads 16.

Additionally, or alternatively, the MRI compatibility information may include information regarding MRI modality 54. In some examples, AIMD 14 may be compatible with certain types of MRI scanners, but may not be compatible with other types of MRI scanners. For example, the AIMD 14 may be compatible with an MRI scanner 55 that produces a magnetic field of a certain approximate field strength level (e.g., 1.5 T) or may be compatible with an MRI scanner 55 that has a certain type of body coil. To determine compatibility between AIMD 14 and MRI scanner 55, the processor may automatically acquire information regarding the MRI scanner 55, such as the model number, registration number, or serial number of MRI scanner 55, a manufacturer of MRI scanner 55, a body coil type of MRI scanner 55, e.g., single or multichannel, or the like. In some examples, the MRI compatibility information regarding MRI modality 54 may also include a magnetic field magnitude produced by MRI scanner 55.

In some examples, the MRI compatibility information may include information regarding a presence of another IMD implanted in patient 12 and, optionally, MRI compatibility information about the other IMD.

In some examples, the processor may not obtain MRI compatibility information regarding the MRI modality 54 to use when determining whether AIMD 14 is compatible with MRI modality 54. For example, the processor may determine that AIMD 14 is not compatible with any MRI modality 54 or that AIMD 14 is compatible with substantially all MRI modalities 54 (i.e., AIMD 14 is MRIS) based on MRI compatibility information regarding AIMD 14 and/or leads 16. However, when the processor determines that AIMD 14 is compatible with an MRI modality 54 having certain characteristics or operating parameters (i.e., that AIMD 14 is MRICS), the processor may automatically obtain information regarding MRI modality 54 to use in determining compatibility between AIMD 14 and the specific MRI modality 54, e.g., based on whether the MRI modality 54 has those characteristics or operating parameters.

As described above with respect to FIG. 4, different aspects of the MRI compatibility information may be stored in memory or a database of different devices within system 50. For example, MRI compatibility information regarding AIMD 14 may be stored in memory 26 of AIMD 14, memory 36 of patient programmer 62 or clinician programmer 64, AIMD data server 60, patient data archive 56, or combinations thereof. Similarly, MRI compatibility information regarding leads 16 may be stored in memory 26 of AIMD 14, memory 36 of patient programmer 62, memory 36 of clinician programmer 64, AIMD data server 60, patient data archive 56, or combinations thereof. MRI compatibility information regarding MRI modality 54 may be stored in a memory of MRI modality 54, MRI data server 58, or combinations thereof.

Although not shown in FIG. 6, in some examples, in addition to obtaining MRI compatibility information automatically from at least two sources (92), the processor may obtain information input by a user, such as patient 12 or a MRI facility staff person or technician, or another medical caregiver. For example, patient 12 may know and remember at least some of the AIMD information or may possess a patient identification or information card with AIMD information printed on the card. Patient 12 may input the information when prompted by the processor (e.g., via patient information terminal 52) or may provide the information to an MRI technician, clinician, or MRI facility staff person, who then enters the data into an appropriate device of system 50. In other examples, patient 12 may possess AIMD Compatibility Documentation produced by a health care provider such as an implanting, managing, or referring physician, which may provide at least some of the MRI compatibility information. Patient 12 may input the information from the AIMD Compatibility Documentation when prompted by the processor (e.g., via patient information terminal 52), or may provide the information to an MRI technician, clinician, or MRI facility staff person to enter the AIMD data into the appropriate device of system 50 when prompted by the processor.

Once the processor has obtained the MRI compatibility information (92), the processor may automatically analyze the MRI compatibility information to determine whether the AIMD 14 is compatible with an MRI modality 54 (74). However, when the MRI compatibility information cannot be obtained (72), such as when some of the necessary MRI compatibility information is not stored in a device interrogated by the processor, further investigation may be necessary or advisable prior to authorizing or refusing the MRI scan (90).

The processor may first analyze information regarding AIMD 14 and leads 16 to determine whether the MRI compatibility information indicates that AIMD 14 is compatible with at least some MRI modalities 54 (i.e., that AIMD 14 is MRICS) or that AIMD 14 is incompatible with substantially all MRI modalities 54. For example, when the MRI compatibility information indicates a presence of an abandoned, orphaned, or broken lead 16 in the body of patient 12, the processor may determine that patient 12 is not a candidate for an MRI scan by MRI modality 54. Similarly, an implant date, model number, registration number, or serial number of AIMD 14 may be utilized as a sort of threshold qualification in determining whether the AIMD 14 comprises MRICS hardware. For example, it may be known that an AIMD 14 implanted prior to a certain date would be incompatible with an MRI modality 54. In this case, the processor may reject as MRI-incompatible a device with a manufacture or implant date prior to a certain date. Conversely, a model number, registration number, or serial number of AIMD 14 may indicate that the AIMD 14 is compatible with substantially all MRI modalities 54 or MRI modalities 54 having certain operating parameters (e.g., certain magnetic field strengths). In this case, the processor may compare the model number, registration number, or serial number to a list of model, registration, or serial numbers associated with AIMDs known to be compatible with a particular MRI modality. In some examples, the processor may execute an algorithm that identifies certain values or patterns of a model number, registration number, or a serial number as corresponding to an AIMD that does or does not comprise MRICS or MRIS hardware. For example, the processor may utilize the first four characters of a model number, registration number, or serial number of AIMD 14 or leads 16 and compare these four characters to a database including entries comprising the first four characters of a plurality of AIMDs or leads. The processor may then make a determination of MRI compatibility of the AIMD 14 based on the results of the comparison of the characters of the serial number, registration number, or model number with entries in the database.

In examples in which the processor determines that AIMD 14 is compatible with some MRI modalities 54, i.e., that AIMD 14 comprises MRICS hardware, the processor may obtain MRI compatibility information regarding the particular MRI modality 54 which is to be used to perform the MRI scan. The processor may then utilize the information regarding the MRI modality 54 (e.g., information regarding MRI scanner 55) to determine whether the AIMD 14 is compatible with the particular MRI modality 54. For example, the processor may determine that AIMD 14 is conditionally compatible with a MRI scanner 55, e.g., AIMD 14 is compatible with an MRI scanner 55 that produces a magnetic field compatible with AIMD 14. The processor may obtain information relating to a magnetic field produced by MRI scanner 55 from MRI modality 54 or MRI data server 58 and may utilize this information to determine whether the AIMD 14 is compatible with the particular MRI scanner 55.

In examples in which the processor determines that AIMD 14 is not compatible with MRI modality 54, the processor may output an indication that AIMD 14 is incompatible with MRI modality 54 and the MRI scan is refused (88). For example, the processor may direct a display or other user interface medium to convey such an indication to a user in a visible, audible or other effective manner. In some examples, the processor may not determine that AIMD 14 is incompatible with MRI modality 54, but the MRI compatibility information that the processor uses to make the compatibility determination may be incomplete, unclear, or conflicting. In these cases, the processor may alert a user of the questionable information, and may refuse to authorize an MRI scan until the information is corrected or provided.

In some examples, once the processor determines that AIMD 14 is compatible with MRI modality 54, the processor may optionally perform one or more safety checks to confirm compatibility between AIMD 14 and MRI modality 54. Two exemplary safety checks are illustrated in FIG. 6 as steps (76) and (78). Although these two safety checks are illustrated as separate steps from determining compatibility between AIMD 14 and MRI modality 54, the steps fall within a broad interpretation of determining compatibility between AIMD 14 and MRI modality 54.

In some examples, the processor optionally may confirm that hardware of AIMD 14 is MRI conditionally safe (MRICS) or MRI safe (MRIS) (76). The processor may confirm that AIMD 14 comprises MRICS or MRIS hardware by obtaining information including, for example, the implant date of AIMD 14, the model number, registration number, or serial number of AIMD 14 and/or leads 16, or the like. In some example, the processor may have already obtained the information as part of step (92) and the processor may utilize the information at this time to confirm AIMD 14 comprises MRICS or MRIS hardware. As described above, such information may be stored in memory 26 of AIMD 14, memory 36 of patient programmer 62 or clinician programmer 64, patient data archive 56, or AIMD data server 60. Additionally or alternatively, the serial number, registration number, or model number of AIMD 14 may be provided on the patient ID card, and patient 12 may input the serial, registration, or model number via patient information terminal 52 or provide the serial or model number to a user, who enters the information in an appropriate device. The processor may use the serial number, registration number, or model number of AIMD 14 and/or leads 16 to retrieve information regarding AIMD 14 or leads 16 from an AMD data server 60, or the like.

In some examples, the processor may execute an algorithm that identifies certain values or patterns of a model number, registration number, or a serial number as corresponding to an AIMD that does or does not comprise MRICS or MRIS hardware. For example, the processor may utilize the first four characters of a model number, registration number, or serial number of AIMD 14 or leads 16 and compare these four characters to a database including entries comprising the first four characters of a plurality of AIMDs or leads. The processor may then make a determination of MRI compatibility of the AIMD 14 based on the results of the comparison of the characters of the serial number, registration number, or model number with entries in the database.

In some examples, the processor may perform a software lockout check to confirm whether AIMD 14 comprises MRICS or MRIS hardware. For example, upon implant of AIMD 14 and leads 16 in patient 12, an implanting physician or another user may communicate the serial number of AIMD 14, serial number of leads 16, and the implant location to a manufacturer of AIMD 14 or a third party, such as a third party that maintains MRICS or MRIS information for various AIMDs. The manufacturer or third party may determine whether the system is MRICS or MRIS based on the serial numbers and the implant location. In some examples, the manufacturer or third party may store the MRICS information for the system in a database on a server, e.g., AIMD data server 60 or patient data archive 56. The software lockout check, then, may include obtaining this information from the AIMD data server 60 or patient data archive 56. In some examples, the processor may also evaluate implant information such as lead location or the presence of abandoned leads to confirm that AIMD 14 comprises MRICS hardware. In some examples, the implant information may be stored in memory 26 of IMD 16 or memory 36 of patient programmer 62 and may be retrieved by the processor.

When the processor completes the step of confirming whether AIMD 14 comprises MRICS or MRIS hardware but determines that AIMD 14 does not comprise MRICS hardware, the processor may generate a notification that AIMD 14 is not compatible with the MRI scanner 55 and patient 12 will not undergo an MRI scan (88).

However, when the processor confirms that AIMD 14 comprises MRICS or MRIS hardware (76), the processor may evaluate MRI compatibility information regarding an implant location of AIMD 14 and leads 16 to confirm that the implant locations permit an MRI scan (78). In some examples, the implant location of AIMD 14 and/or leads 16 may be stored in memory in AIMD 14, external programmer 20, patient data archive 56, AIMD data server 60, or the like. In some examples, the processor may automatically obtain the implant location information from one or more of patient programmer 62, AIMD 14, clinician programmer 64, AIMD data server 60, or patient data archive 56, while in other examples, a user may input the implant location information, e.g., via patient information terminal 52, or the like.

In some examples, a user may determine the AIMD implant location or MRICS hardware exceptions by x-ray images or fluoroscopic images. For example, the x-ray or fluoroscopic images may show an abandoned lead, i.e., a lead that is not coupled to an IMD, or a lead that is broken or damaged. The AIMD implant location or MRICS hardware exceptions (e.g., abandoned leads) may then be stored in a memory of a device in system 50, as described above.

Some locations at which AIMD 14 or leads 16 are implanted may preclude patient 12 from having an MRI scan. For example, leads 16 may be implanted proximate to a particular anatomical target of the patient 12, or near a target that does not correspond to a customary implant location. Similarly, leads 16 that are orphaned, i.e., unconnected to a stimulator, or damaged may preclude patient 12 from having an MRI scan due to potential overheating of the leads 16. When the processor determines that AIMD 14 is implanted in a location that precludes an MRI scan or patient 12 has implanted leads 16 that have become damaged or orphaned (78), the processor may generate a notification to a user that patient 12 should not undergo an MRI scan (88).

When the processor determines that the AIMD 14 is implanted in a location that does not preclude an MRI scan and patient 12 does not have any implanted leads that are damaged or orphaned, the processor may proceed to transmit an instruction to processor 24 of AIMD 14 to prepare for an AIMD scan or may prompt the user to prepare AIMD 14 for an MRI scan (80). In some examples, the processor may transmit an instruction to processor 24 to perform a lead impedance test for each lead 16A, 16B (and, if present, any lead extensions or adaptors) that is coupled to AIMD 14. The impedance test may be an open/close test that indicates whether any of leads 16 includes a broken conductor, which may produce an open circuit. The impedance test also may indicate presence of contact between two conductors, which results in a short circuit. In some examples, when the impedance test indicates an open circuit or a short circuit, processor 24 may transmit an indication to the processor, which may then generate a notification to the user that patient 12 cannot undergo an MRI scan (88).

However, when the impedance test indicates that the leads 16 are functional and AIMD 14 is functioning correctly, the processor may proceed to ensure that AIMD 14 is in an MRICS mode. In some examples, AIMD 14 may permanently be in an MRICS mode, and the processor may not transmit any instruction to processor 24 adjust AIMD 14 in any way. In other examples, the processor may transmit an instruction to processor 24 to enter an MRI mode, e.g., using patient programmer 62 or clinician programmer 64. The MRICS mode may include features that prevent AIMD 14 from inadvertently delivering stimulation to patient 12 during the MRI scan. For example, the MRICS mode may place AIMD 14 in a low power state in which AIMD 14 does not deliver stimulation, but which prevents accidental provision of stimulation to patient 12. In some examples, AIMD 14 may be providing life-sustaining therapy, and may not be able to be placed in an MRICS mode in which stimulation is interrupted. In these examples, the processor may indicate this fact to the user, and the user may inform patient 12 that he or she should not undergo an MRI scan (88).

When the processor has prepared AIMD 14 for the MRI scan (80), the processor may transmit instructions to MRI modality 54 to prepare the MRI scanner 55 or may prompt the user to prepare the MRI scanner 55 for scanning (82). Preparation of the MRI scanner 55 for scanning may include, for example, scan parameter validation, e.g., setting or confirming MRI scan parameters according to which the MRI scanner 55 will scan patient 12. The MRI scan parameters may include, for example, a magnetic field magnitude and a gradient strength. A magnetic field that is too high may not be suitable for a patient 12 having an AIMD 14 implanted in his or her body, as described above. Similarly, a gradient strength that is too large may not be suitable for a patient having an AIMD 14 implanted in his or her body.

In some examples, the processor may transmit an instruction or set of instructions that instruct MRI modality 54 to set MRI scan parameters. In other examples, a user, such as a clinician or MRI technician, may be responsible for setting and confirming the MRI scan parameters. The user may confirm that the MRI scan parameters adheres to the guidelines of the AIMD 14 implanted in patient 12. In some examples, the user may consult a radiologist or a manufacturer of AIMD 14 for assistance in setting the MRI scan parameters. For example, the user may contact the manufacturer of AIMD 14 via a phone call or a website of the manufacturer.

The processor or the user may also confirm that the RF coil of the MRI scanner 55 is compatible with AIMD 14. For example, AIMD 14 may be compatible only with an MRI scanner 55 that include a single channel RF coil, and may not be compatible with an MRI scanner 55 that includes a multiple channel RF coil. As another example, a quadrature bird cage RF coil may function in linear mode and cause AIMD 14 to be exposed to an excessive magnetic field.

In some examples, the MRI scanner 55 may include an AIMD mode that assures stringent internal limits on operation of the MRI scanner 55 to prevent AIMD 14 from being exposed to excessive magnetic fields. The processor or the user may configure the MRI scanner 55 in the AIMD mode prior to scanning patient 12. Once the MRI scanner 55 is prepared for scanning (82), a user may initiate the MRI scan of patient 12 (84).

Finally, regardless of whether the previous steps of the technique resulted in an MRI scan of patient 12 or a notification that patient 12 cannot undergo an MRI scan, the information collected in the preceding steps and the results of the determinations made by the processor may be archived in patient data archive 56 (86). Additionally or alternatively, the patient data archive 56 may serve as a location from which MRI compatibility information may be obtained at a later time. As described above, patient data archive 56 may comprise a database of information regarding a plurality of patients, which may be maintained by the MRI facility, an organization with which the MRI facility is associated, or a third party. In some examples patient data archive may include an electronic and/or printed copy of the information collected and the determinations made by system 50 or a user. For example, some or all of the information collected in the various steps of the technique illustrated in FIG. 6 may be stored in a Digital Imaging and Communications in Medicine (DICOM) Modality Worklist record, which may be subsequently available to MRI technicians or other clinician.

Figure 7:
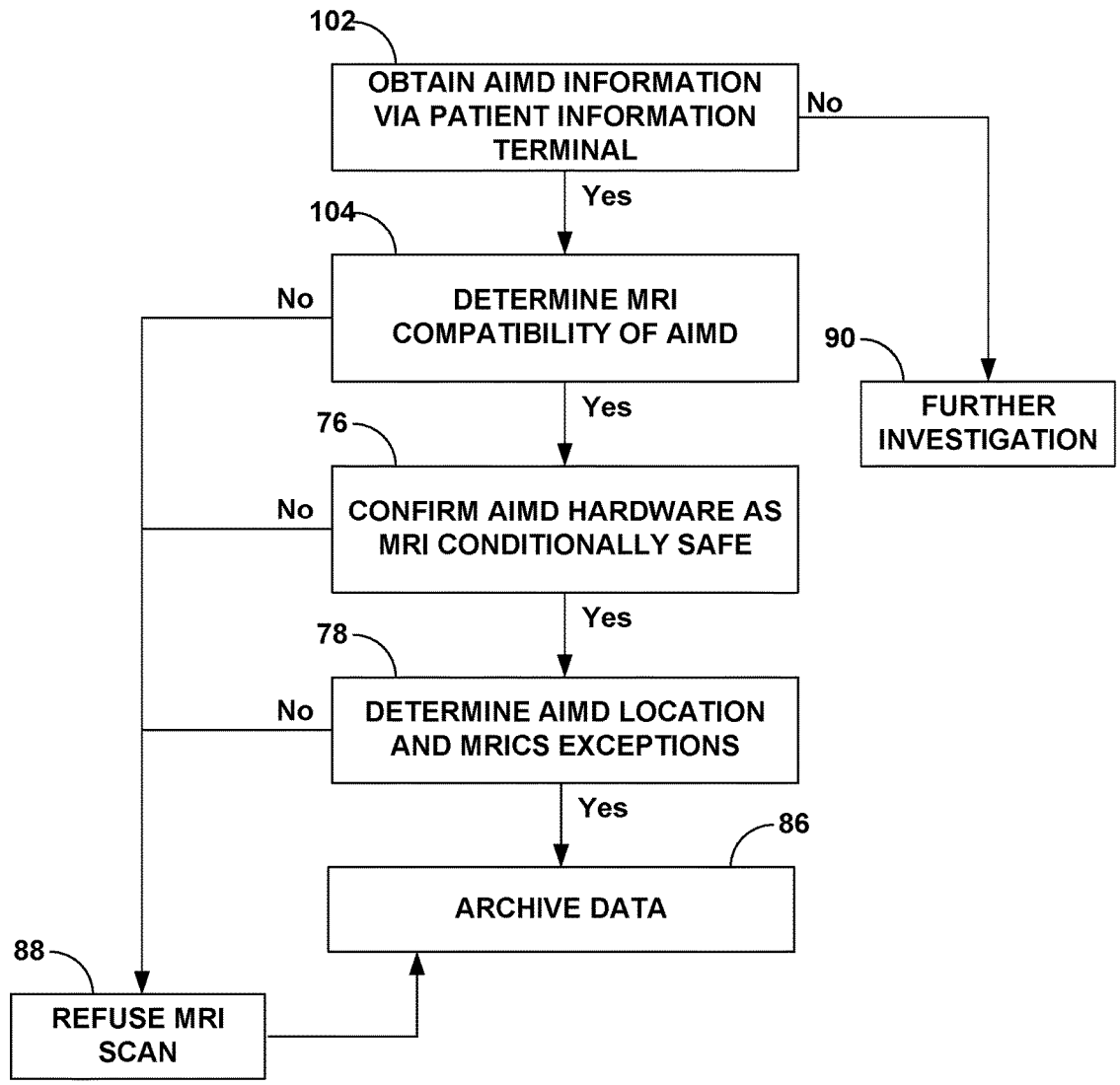
FIG. 7 is a flow diagram illustrating another example of a technique for determining compatibility of an AIMD and an MRI modality.

FIG. 7 is a flow diagram that illustrates another technique according to which a determination of compatibility between an AIMD 14 and a MRI modality 54 may be made. While the technique illustrated in FIG. 6 was directed to an automated or partially automated technique executed by a processor for determining compatibility between an AIMD 14 and an MRI modality 54, the technique illustrated in FIG. 7 is directed to a patient-centric technique for obtaining information relevant to compatibility between an AIMD 14 and an MRI modality 54. In some examples, the patient-centric technique illustrated in FIG. 7 may be more efficient than another technique for determining compatibility between an AIMD 14 and an MRI modality 54. For example, the patient-centric technique illustrated in FIG. 7 may allow a patient 12 to enter information regarding an AIMD 14 implanted in the body of the patient 12 and determine whether the AIMD is compatible with an MRI modality 54. Additionally, a patient-centric technique may empower a patient 12 to better appreciate and understand why the patient 12 does or does not qualify for an MRI scan, and may enable the patient 12 to make more informed decisions regarding his or her care. In some examples, the results of the patient-centric technique illustrated in FIG. 7 may be verified by a physician prior to performing an MRI scan or may be supplemented by another technique illustrated herein to verify that the information provided by the patient 12 is correct and consistent.

The technique illustrated in FIG. 7 may be primarily implemented in a patient information terminal 52. As described above, patient information terminal 52 may include a laptop computer, a desktop computer, or a workstation that executes a software program or accesses a website that guides the patient to enter information pertinent to the determination of compatibility of AIMD 14 and AIMD modality 54. Hence, patient information terminal 52 may be a hardware device that resides in an MRI facility or clinic for direct access by a patient 12, and/or a hardware device that includes, is coupled to or otherwise provides a web server or other remote server that presents a user interface for remote access by the patient. Patient 12 may enter the MRI compatibility information via patient information terminal 52 at his or her convenience prior to an MRI appointment. For example, patient 12 may access a website presented by a web server from a personal computer located at his or her home or another location. Web pages provided by the web server may present a front end interface for a patient 12 operating a patient computer to obtain remote access to patient information terminal 52, e.g., via network 66. Alternatively, the patient may access patient information terminal 52 directly in the MRI facility or clinic. The website may prompt patient 12 to enter MRI compatibility information, and may guide patient 12 through entry of the MRI compatibility information. For example, the website may include illustrations or other aids that assist patient 12 in retrieving the MRI compatibility information from his or her patient ID card, AIMD Compatibility Documentation, patient programmer 62, or AIMD 14 via the patient programmer 62. In some cases, the website may be presented by MRI compatibility web server 68 or by some other web server.

Patient information terminal 52 may execute a software program or access a website such as a website provided by MRI compatibility server 68, which provides instructions regarding the MRI compatibility information to be obtained from patient 12. For example, patient information terminal 52 may execute an application program that executes locally on patient information terminal 52 or remotely via network 66 and prompts patient 12 to input pertinent information. The program may additionally evaluate the information entered by patient 12 and present subsequent prompts to patient 12 based on previously entered information. In some examples, the program executed by patient information terminal 52 may automatically determine whether the AIMD 14 is compatible with an MRI modality 54, while in other examples, the program may provide an output that patient 12 may provide to a user, such as a clinician or MRI technician, who may then determine whether AIMD 14 is compatible with the MRI modality 54.

In the example technique illustrated in FIG. 7, patient information terminal 52 first obtains MRI compatibility information from patient 12 via patient information terminal 52 (102). As described above, the MRI compatibility information may include, for example, a date on which AIMD 14 was implanted in patient 12 or a date on which a revision was made to AIMD 14. The revision may include, for example, a subsequent surgical procedure to repair or modify AIMD 14 or a surgical procedure to replace, modify, or implant leads 16 that connect to AIMD 14. In some examples, the MRI compatibility information may include an indication of a presence of another IMD implanted in patient 12. The MRI compatibility information also may include a name and/or phone number of a physician who implanted AIMD 14 in patient 12 or who manages therapy provided to patient 12 by AIMD 14. In some examples, the MRI compatibility information also includes a manufacturer of AIMD 14 and/or leads 16, contact information for the manufacturer, or a serial number, registration number, or model number of AIMD 14 and/or leads 16. The MRI compatibility information may optionally also include information regarding a location at which AIMD 14 is implanted in patient 12, such as, for example, torso, right or left leg, cranium, or more specific location information.

In some examples, at least some of the MRI compatibility information may be stored on a patient ID card or AIMD Compatibility Documentation. Patient 12 may carry the patient ID card as a reference for the information contained thereon, and may refer to the patient ID when entering the MRI compatibility information via patient information terminal 52.

AIMD Compatibility Documentation may also contain at least some of the information discussed above in this disclosure. The AIMD Compatibility Documentation may have been produced recently by a health care provider, such as an implanting, managing, or referring physician, based on the health care provider's knowledge of the MRI compatibility of AIMD 14. AIMD Compatibility Documentation may be possessed by patient 12 and referred to when entering pertinent data into patient information terminal 52.

In some examples, at least some of the MRI compatibility information may be stored in memory 36 of patient programmer 62. As described above, patient 12 may use patient programmer 62 to interact with AIMD 14. In some examples, patient programmer 62 may allow patient 12 to select among a number of available therapy programs stored in memory 36 of patient programmer or memory 26 of AIMD 14 or to adjust one or more therapy parameter of a therapy program within a range determined by a clinician and stored in memory 26 or memory 36. Patient programmer 62 may be carried by patient 12 and may be portable such that patient programmer 62 may accompany patient 12 through his or her daily routine. In some examples, the patient 12 may retrieve information from memory 36 of patient programmer 62 via user interface 38 of patient programmer 62. In some examples, the information stored in memory 36 of patient programmer 62 may include, for example, one or more of implant date or revision date, physician name and/or telephone number, manufacturer name, model number, registration number, or serial number of AIMD 14 and/or leads 16, an implant location, compatible magnetic field strength, or the like.

In other examples, at least some of the MRI compatibility information may be stored in memory 26 of AIMD 14. Information stored in memory 26 may be retrieved by via patient programmer 62 or clinician programmer 64, e.g., via wireless telemetry. Patient 12 may then view the MRI compatibility information and enter the information via patient information terminal 52. Memory 26 may store, for example, one or more of implant date or revision date, physician name and/or telephone number, manufacturer name, model number, registration number, or serial number of AIMD 14 and/or leads 16, implant location, compatible magnetic field strength, or the like. In some examples, at least some of the information may be stored in memory 26 of AIMD 14 while at least some of the information is stored in memory 36 of patient programmer 62. Some of the same information may be stored in memory 26 and memory 36 in some cases.

In some examples, patient information terminal 52 may be configured to supplement the MRI compatibility information provided by patient 12 with MRI compatibility information retrieved from another device in system 50, such as, for example, AIMD data server 60, MRI data server 58, patient data archive 56, MRI modality 54, or the like. In some cases, when patient 12 indicates that he or she does not know or is unable to obtain MRI compatibility information requested by patient information terminal 52, the software program or web page executed by patient information terminal 52 may automatically attempt to obtain the requested information from one or more of AIMD data server 60, MRI data server 58, patient data archive 56, and/or MRI modality 54. In other examples, patient information terminal 52 may not attempt to retrieve MRI compatibility information from another device of system 50, and may instead indicate to patient 12 that an MRI compatibility determination cannot be made with the available information and further investigation is required (90).

Once the MRI compatibility information has been collected (102), patient information terminal 52 determines compatibility of AIMD 14 and an MRI modality 54 (104). In some examples, patient information terminal 52 may not have collected any information regarding a particular MRI modality 54 at this time. Instead, patient information terminal 52 may provide a general indication to patient 12 based on the MRI compatibility information regarding AIMD 14 and/or leads 16 whether AIMD 14 is MRI compatible. For example, patient information terminal 52 may analyze the implant date of AIMD 14 and/or leads 16 to determine whether AIMD is MRI compatible. For example, it may be known that an AIMD 14 implanted prior to a certain date would not be MRI compatible (i.e., that the AIMD would not comprise MRICS or MRIS hardware).

In some examples, patient information terminal 52 may utilize a serial number, registration number, or model number of AIMD 14 and/or leads 16 coupled to AIMD 14 to determine whether AIMD 14 is MRI compatible. Patient information terminal 52 may use the serial number, registration number, or model number of AIMD 14 and leads 16 to retrieve information regarding MRI compatibility of AIMD 14 or leads 16 from a spreadsheet or database of serial number or model numbers and corresponding MRI compatibility or MRI incompatibility. The spreadsheet or database may be stored in, for example, patient information terminal 52 or MRI compatibility web server 68. In some examples, patient information terminal 52 may utilize the serial number, registration number, or model number to retrieve data regarding the AIMD from AIMD data server 60.

In some examples, patient information terminal 52 may execute an algorithm that identifies certain values or patterns of a model number, registration number, or a serial number as corresponding to an AIMD 14 that does or does not comprise MRICS or MRIS hardware. For example, patient information terminal 52 may utilize the first four characters of a model number, registration number, or serial number of AIMD 14 or leads 16 and compare these four characters to a database including entries comprising the first four characters of a plurality of AIMDs or leads. Patient information terminal 52 may then make a determination of MRI compatibility of the AIMD 14 based on the results of the comparison of the characters of the serial number, registration number, or model number with entries in the database.

Based on the MRI compatibility information regarding AIMD 14 and/or leads 16, patient information terminal 52 may determine whether AIMD 14 is compatible with substantially all MRI modalities 54 (i.e., is MRI safe), whether AIMD 14 is compatible with MRI modalities 54 having certain operating parameters or characteristics (i.e., is MRI conditionally safe), or whether AIMD 14 is incompatible with substantially all MRI modalities (104). When patient information terminal 52 determines that AIMD 14 is incompatible with substantially all MRI modalities, patient information terminal 52 may generate and display a notification to patient 12 that he or she does not qualify for an MRI scan (88). When patient information terminal 52 determines that AIMD 14 is compatible with at least some MRI modalities (54), patient information terminal 52 may proceed to confirm that AIMD 14 comprises MRICS or MRIS hardware (76).

In some examples, AIMD 14 may be compatible with certain types of MRI modalities, but may not be compatible with other types of MRI modalities (i.e., may be MRI conditionally safe). To determine compatibility between AIMD 14 and an MRI modality 54 with more specificity, patient information terminal 52 may obtain MRI compatibility information regarding the MRI modality 54 prior to determining MRI compatibility of AIMD 14 (104). For example, patient information terminal 52 may obtain information regarding MRI modality 54 via network 66 from MRI modality 54, MRI data server 58, or the like. The MRI compatibility information regarding MRI modality may include, for example, the type of MRI scanner 55, the RF coil type, and the like. In some examples, the type of MRI scanner 55 may include the model number and manufacturer of the MRI scanner 55. In other examples, the type of MRI scanner 55 may include the magnet type and the magnetic field strength produced by the MRI scanner 55. For example, an AIMD 14 may be compatible with an MRI scanner 55 that produces a magnetic field having a magnitude of 1.5 T. In other examples, the magnetic field with which AIMD 14 is compatible may be different. The RF coil type may include an indication of whether the RF coil is a single channel or a multiple channel RF coil.

Patient information terminal 52 may compare the information regarding MRI modality 54 and the information regarding AIMD 14 to determine whether AIMD 14 is compatible with the MRI modality 54. Patient information terminal 52 may automatically determine whether AIMD 14 and MRI modality 54 are compatible based on the MRI modality information and the AIMD information.

For example, patient information terminal 52 may compare a magnetic field strength with which AIMD 14 is compatible to a magnetic field, e.g., a magnetic field or a magnetic field produced by a particular set of MRI scan parameters, produced by MRI scanner 55. When patient information terminal 52 determines that AIMD 14 is not compatible with MRI modality 54, patient information terminal 52 outputs an indication that AIMD 14 is incompatible with MRI modality 54 and the MRI scan is refused (88). In some examples, patient information terminal 52 may not determine that AIMD 14 is incompatible with MRI modality 54, but one or both of the AIMD information or the MRI modality information may be incomplete, unclear, or conflicting. In these cases, patient information terminal 52 may alert patient 12 of the questionable information, and may refuse to authorize MRI scan until the information is corrected or provided.

In some examples, once patient information terminal 52 determines that AIMD 14 is compatible with MRI modality 54, patient information terminal 52 optionally may proceed to confirm that AIMD 14 comprises MRICS or MRIS hardware (76) as a safety measure. Patient information terminal 52 may confirm that the AIMD 14 comprises MRICS or MRIS hardware by collecting information including, for example, the implant date of AIMD 14, the model number, registration number, or serial number of AIMD 14 and/or leads 16, or the like. In some example, patient information terminal 52 may have obtained at least some of this information when obtaining MRI compatibility information (102), while in other examples, patient information terminal 52 may prompt patient 12 to enter at least some of this information at this time, or may obtain at least some of the information from another device in system 50 at this time. In some examples, the implant date may be utilized as a sort of threshold qualification in determining whether the implant comprises MRICS or MRIS hardware. For example, it may be known that an AIMD 14 implanted prior to a certain date would not have included MRICS or MRIS hardware. In some examples, patient information terminal 52 may utilize the serial number, registration number, or model number of AIMD 14 and leads 16 to retrieve information regarding AIMD 14 or leads 16 from an AMD data server 60, a manufacturer's website, a third party website, or the like.

In some examples, patient information terminal 52 may execute an algorithm that identifies certain values or patterns of a model number, registration number, or a serial number as corresponding to an AIMD 14 that does or does not comprise MRICS or MRIS hardware. For example, patient information terminal 52 may utilize the first four characters of a model number, registration number, or serial number of AIMD 14 or leads 16 and compare these four characters to a database including entries comprising the first four characters of a plurality of AIMDs or leads. Patient information terminal 52 may then make a determination of MRI compatibility of the AIMD 14 based on the results of the comparison of the characters of the serial number, registration number, or model number with entries in the database.

The information used by patient information terminal 52 to confirm that AIMD 14 comprises MRICS or MRIS hardware also may include a software lockout check. In some examples, upon implantation of AIMD 14 and leads 16, an implanting physician or another user may communicate the serial number of AIMD 14, serial number of leads 16, and the implant location to a manufacturer of AIMD 14 or a third party, such as a third party that maintains MRICS information for various AIMDs. The manufacturer or third party may determine whether AIMD 14 is MRICS or MRIS based on the serial numbers and the implant location. In some examples, the manufacturer or third party may issue a MRICS card that indicates that AIMD 14 and leads 16 do or do not form an MRICS system to patient 12, may issue a patient ID card with an indication that AIMD 14 and leads 16 do or do not form an MRICS or MRIS system, or may store the MRICS information for the system in a database on a server, e.g., AIMD data server 60 or patient data archive 56. The software lockout check, then, may include obtaining this information from the MRICS card, the patient ID card, or the database. In some examples, a manufacturer of AIMD 14 may provide a blank MRICS card to the implanting physician, who may fill out the MRICS card with, for example, a serial number of AIMD 14 and/or leads 16, and implant location of AIMD 14 and/or leads 16, or an indication of whether the system formed by AIMD 14 and leads 16 is MRICS or MRIS. When patient information terminal 52 determines that AIMD 14 does not comprise MRICS or MRIS hardware, patient information terminal 52 may generate a notification that AIMD 14 is not compatible with the MRI modality 54 and patient 12 will not undergo an MRI scan (88).

When patient information terminal 52 determines that AIMD 14 does, in fact, comprise MRICS or MRIS hardware, patient information terminal 52 optionally may proceed to prompt patient 12 to input the AIMD location and any MRICS hardware exceptions (78) as another safety check. In some examples, patient 12 may determine the AIMD implant location or MRICS hardware exceptions by retrieving information stored in memory 26 of AIMD 14 or memory 36 of patient programmer 62 or by a phone call to the manufacturer of AIMD 14. In other examples, patient information terminal 52 may retrieve the information from AIMD data server 60 or by accessing a website of the manufacturer. In some examples, retrieving the information from the manufacturer may require the serial number of AIMD 14, and may only work when AIMD 14 has been registered with the manufacturer.

Some locations at which AIMD 14 or leads 16 are implanted may preclude patient 12 from having an MRI scan. For example, leads 16 may be implanted proximate to a particular anatomical target of the patient 12, or near a target that does not correspond to a customary implant location. Similarly, leads 16 that are orphaned, i.e., unconnected to a stimulator, or damaged may preclude patient 12 from having an MRI scan due to potential overheating of the leads 16. When patient information terminal 52 determines that AIMD 14 is implanted in a location that precludes an MRI scan or patient 12 has implanted leads 16 that are damaged or orphaned, patient information terminal 52 may generate a notification to a user that patient 12 cannot undergo an MRI scan (88).

Regardless of whether the previous steps of the technique resulted in an MRI scan of patient 12 or a notification that patient 12 cannot undergo an MRI scan, the information collected in the preceding steps and the results of the determinations made by patient information terminal 52 may be archived in patient data archive 56 (86). As described above, patient data archive 56 may comprise database of information regarding a plurality of patients, which may be maintained by the MRI facility, an organization with which the MRI facility is associated, or a third party. In some examples patient data archive may include an electronic and/or printed copy of the information collected and the determinations made by system 50 or a user. In some examples, some or all of the information collected in the various steps of the technique illustrated in FIG. 7 may be stored in a Digital Imaging and Communications in Medicine (DICOM) Modality Worklist record, which may be subsequently available to MRI technicians or other clinician.

While the examples illustrated in FIGS. 5-7 have concerned obtaining MRI compatibility information and determining compatibility between an AIMD 14 and an MRI modality based on the MRI compatibility information, in some examples, the MRI compatibility information may have been previously obtained. For example, it may be desired that patient 12 has the ability to determine compatibility of AIMD 14 with an MRI modality 54, and when it is determined that AIMD 14 is compatible with the MRI modality 54, to configure AIMD 14 in a MRI conditionally safe operating mode. To facilitate such a MRI compatibility determination and configuration of AIMD 14, patient 12 may utilize a patient programmer 62. As described above, a patient programmer 62 may be a portable device that generally accompanies the patient throughout a daily routine. Patient 12 may possess patient programmer 62 and utilize the patient programmer 62 to interact with AIMD 14, e.g., to retrieve information from AIMD 14 or to program AIMD 14 within limits prescribed by a managing physician.

Figure 8:
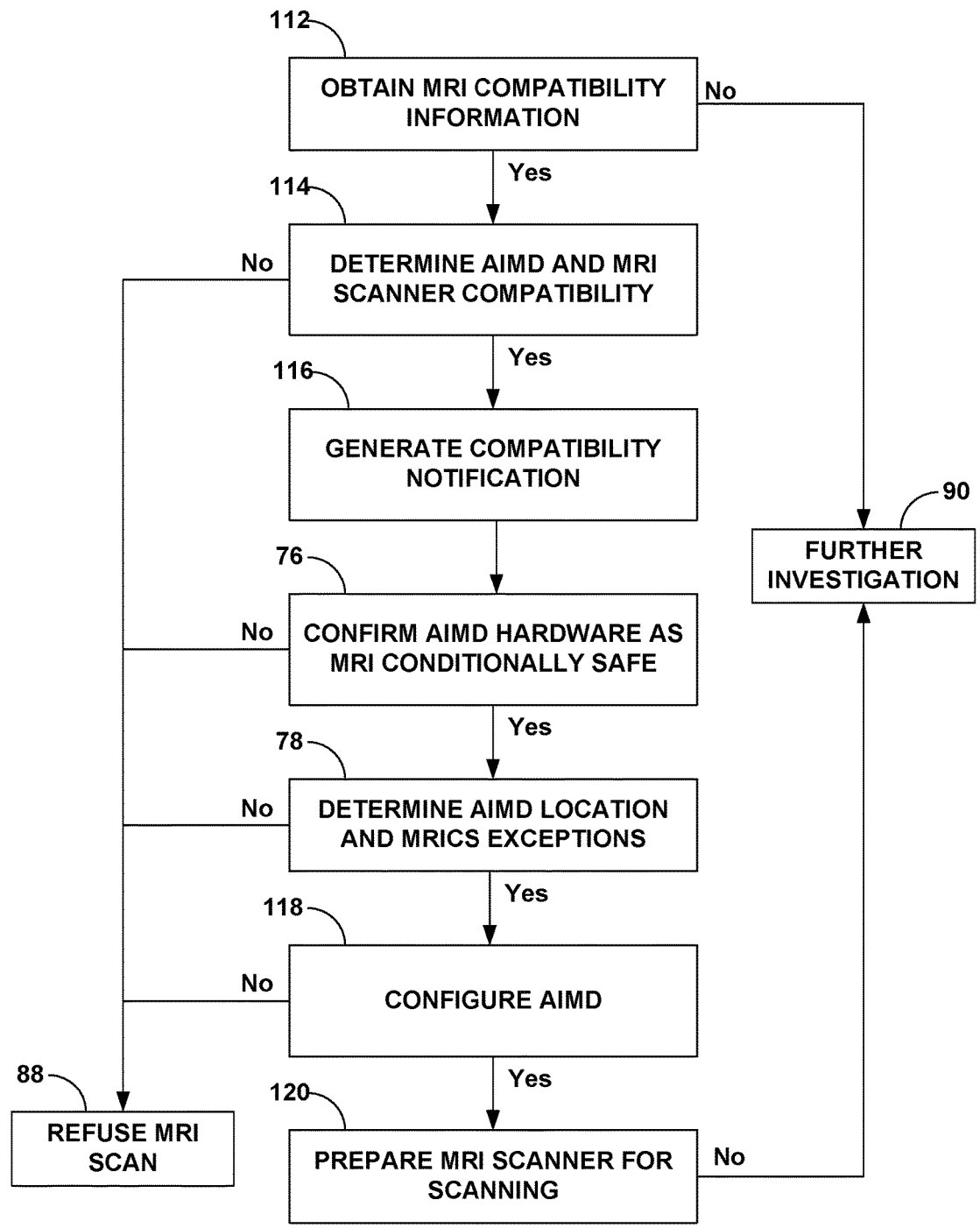
FIG. 8 is a flow diagram illustrating another example of a technique for determining compatibility of an AIMD and an MRI modality.

In some examples, patient programmer 62 may implement software, hardware, firmware, or combinations thereof that enable patient programmer 62 to automatically obtain from memory 26 of AIMD 14 and/or memory 36 of patient programmer 62 information regarding MRI compatibility of AIMD 14. In some examples, patient programmer 62 may utilize the MRI compatibility information to make a determination of MRI compatibility of AIMD 14. Patient programmer 62 may then display the results of the determination of MRI compatibility via user interface 38, or may communicate the MRI compatibility determination results to another computing device in system 50 (FIG. 4), such as patient information terminal 52, clinician programmer 64, MRI modality 54, or the like, for display to a user, such as patient 12, a clinician, or an MRI technician. In other examples, patient programmer 62 may communicate the MRI compatibility information to another computing device in computing system 50, and the other computing device may make the MRI compatibility determination. Additionally, patient programmer 62 may implement software, hardware, firmware, or combinations thereof that enable the programmer 62 to instruct AIMD 14 to enter an MRI conditionally safe operating mode. FIG. 8 illustrates an example of a technique that may be implemented by the patient programmer. The technique illustrated in FIG. 8 will be described with reference to AIMD 14 of FIG. 2 and patient programmer 62 of FIG. 4, which may include components similar to those of external programmer 20 of FIG. 3.

According to the technique illustrated in FIG. 8, processor 34 of patient programmer 62 first obtains MRI compatibility information (112). In some examples, processor 34 of patient programmer 62 interrogates AIMD 14 to retrieve MRI compatibility information stored in AIMD 14. In particular, the MRI compatibility information may be stored in memory 26 of AIMD 14. As described above, memory 26 may store, for example, an implant date of AIMD 14 and/or leads 16, a revision date, if any, of AIMD 14 and/or leads 16, or a name and/or phone number of a physician who implanted AIMD 14 or manages care of patient 12. In some examples, memory 26 may store an indication of a presence of another IMD implanted in patient 12. In some examples, memory 26 may store a manufacturer of AIMD 14 and contact information for the manufacturer, a serial, registration, or model number or name of AIMD 14 and/or leads 16, and/or a magnetic field magnitude to which AIMD 14 can be exposed. Additionally or alternatively, memory 26 may store information regarding an implant location of AIMD 14 and/or leads 16, an indication of the presence of an abandoned, broken, or damaged lead 16, or an impedance of one or more of leads 16.

In some examples, in addition or as an alternative to interrogating AIMD 14 to obtain the MRI compatibility information, processor 34 of patient programmer 62 may obtain MRI compatibility information stored in memory 36 of patient programmer 62. Memory 36 of patient programmer 62 may store any of the MRI compatibility information described above as being stored in memory 26 of AIMD 14, or any other applicable MRI compatibility information. For example, the MRI compatibility information may be stored in memory 36 of programmer 62 as a result of a previous interrogation of memory 26 of AIMD 14, or as a result of storage of the MRI compatibility information in memory 36 of programmer 62 by a clinician or other caregiver. In some examples, some of the MRI compatibility information may be stored in memory 26 of AIMD 14 and some of the compatibility information may be stored in memory 36 of patient programmer 62, and processor 34 may retrieve MRI compatibility information from both sources.

The MRI compatibility information may have been programmed into memory 26 of AIMD 14 and/or memory 36 of patient programmer 62 at the time of manufacture or upon implantation of AIMD 14 in patient 12. For example, the model number, registration number, or serial number of AIMD 14, a manufacturer of AIMD 14, contact information for the manufacturer, or a magnetic field magnitude to which AIMD 14 can be exposed may be stored in memory 26 and/or memory 36 at the time of manufacture of AIMD 14. As another example, at the time of implant of AIMD 14, the implanting physician may program into memory 26 and/or memory 36 an implant date of AIMD 14 and leads 16, a name and/or phone number of the implanting physician, a serial, registration, or model number or name of AIMD 14 and/or leads 16, an implant location of AIMD 14 and/or leads, or the like.

In some examples, when a change is made to AIMD 14 or leads 16, the MRI compatibility information stored in memory 26 and/or memory 36 may be updated. For example, an implanting physician may update the MRI compatibility information stored in memory 26 and/or memory 36 when a revision is made to AIMD 14 or leads 16 or when a broken, abandoned, or damaged lead 16 is discovered. In some examples, AIMD 14 may automatically update at least some of the MRI compatibility information when AIMD 14 determines or discovers that the MRI compatibility has changed, e.g., upon measuring an impedance of leads 16 and determining the impedance has changed from a previous measurement.

In examples in which processor 34 obtains MRI compatibility information from AIMD 14, such as patient 12, processor 34 of patient programmer 62 may generate an instruction requesting processor 24 of AIMD 14 to transmit the MRI compatibility information stored in memory 26 to processor 34 in response to an input from a user, such as patient 12. Processor 34 may then communicate the instruction via telemetry circuit 40 to telemetry circuit 28 and processor 24 of AIMD 14. Processor 24 of AIMD 14 then may retrieve the MRI compatibility information from memory 26 and communicate the information via telemetry circuit 28 to telemetry circuit 40 and, ultimately, processor 34 of patient programmer 20.

In some examples, once processor 34 of patient programmer 62 has obtained the MRI compatibility information (112), processor 34 may automatically analyze the MRI compatibility information to determine whether the AIMD 14 is compatible with an MRI modality 54 (114). However, when the MRI compatibility information cannot be obtained, such as when some of the necessary MRI compatibility information is not stored in memory 26 of AIMD 14, processor 34 of patient programmer 62 may output an indication via user interface 38 that further investigation is necessary prior to authorizing or refusing the MRI scan (90).

In examples in which sufficient MRI compatibility information is stored in memory 26 of AIMD 14 and/or memory 36 of patient programmer 62, processor 34 may utilize the MRI compatibility information to determine whether the AIMD 14 is compatible with an MRI modality 54 (114). In some examples, processor 34 may not have collected any information regarding a particular MRI modality 54 at this time. Instead, processor 34 may provide a general indication to patient 12 based on the MRI compatibility information regarding AIMD 14 and/or leads 16 whether AIMD 14 is compatible with an MRI modality 54 and, optionally, operating parameters of MRI modality 54 with which AIMD 14 is compatible. For example, processor 34 of patient programmer 62 may analyze the implant date of AIMD 14 and/or leads 16 to determine whether AIMD is MRI compatible. For example, it may be known that an AIMD 14 implanted prior to a certain date would not be MRI compatible (i.e., would not comprise MRICS or MRIS hardware).

In some examples, processor 34 may utilize a serial number, registration number, or model number of AIMD 14 and/or leads 16 coupled to AIMD 14 to determine whether AIMD 14 is MRI compatible. Processor 34 may use the serial number, registration number, or model number of AIMD 14 and leads 16 to retrieve information regarding MRI compatibility of AIMD 14 or leads 16 from a spreadsheet or database of serial numbers, registration numbers, or model numbers and corresponding MRI compatibility or MRI incompatibility. The spreadsheet or database may be stored in, for example, memory 36 of patient programmer 62.

In some examples, processor 34 may execute an algorithm that identifies certain values or patterns of a model number, registration number, or a serial number as corresponding to an AIMD 14 that does or does not comprise MRICS or MRIS hardware. For example, processor 34 may utilize the first four characters of a model number, registration number, or serial number of AIMD 14 or leads 16 and compare these four characters to a database including entries comprising the first four characters of a plurality of AIMDs or leads. Processor 34 may then make a determination of MRI compatibility of the AIMD 14 based on the results of the comparison of the characters of the serial number, registration number, or model number with entries in the database.

Based on the MRI compatibility information regarding AIMD 14 and/or leads 16, processor 34 of patient programmer 62 may determine whether AIMD 14 is compatible with substantially all MRI modalities 54 (i.e., is MRI safe), whether AIMD 14 is compatible with MRI modalities 54 having operating parameters or characteristics (i.e., is MRI conditionally safe), or whether AIMD 14 is incompatible with substantially all MRI modalities (114). For example, an AIMD 14 may be compatible with an MRI modality 54 that produces a magnetic field strength of approximately 1.5 T, or some other specified level, or may be compatible with an MRI modality 54 having only certain types of RF coils, e.g., a single channel RF coil or a multichannel RF coil. When processor 34 determines that AIMD 14 is incompatible with substantially all MRI modalities, processor 34 may generate and display a notification via user interface 38 to patient 12 that he or she does not qualify for an MRI scan (88).

When processor 34 of patient programmer 62 determines that AIMD 14 is compatible with at least some MRI modalities (114), e.g., an MRI modality 54 producing a magnetic field of approximately 1.5 T, processor 34 of patient programmer 62 may generate a notification of such compatibility (116). In some examples, the notification may include information regarding the type of MRI modality 54 or operating parameters of MRI modality with which AIMD 14 is compatible. In some examples, processor 34 may cause the notification to be displayed or otherwise output via user interface 38 of patient programmer 62, while in other examples, processor 34 may transmit the notification to another computing device in system 50, e.g., patient information terminal 52, MRI modality 54, MRI compatibility web server 68, or the like, which then displays the notification to a user, such as patient 12, a clinician, or an MRI technician.

In some examples, when processor 34 determines that AIMD 14 is compatible with at least some MRI modalities (114), processor 34 may proceed to obtain information regarding the specific MRI modality 54 which is to be used to perform the desired MRI scan on patient 12. Processor 34 may then utilize the information regarding the MRI modality 54 (e.g., information regarding MRI scanner 55) to determine whether the AIMD 14 is compatible with the particular MRI modality 54. For example, processor 34 may determine that AIMD 14 is conditionally compatible with an MRI scanner 55, e.g., AIMD 14 is compatible with MRI scanner 55 when MRI scanner 55 is configured to produce a magnetic field compatible with AIMD 14. Processor 34 may obtain information relating to a magnetic field produced by MRI scanner 55 from MRI modality 54 or MRI data server 58 and may utilize this information to determine whether the AIMD 14 is compatible with the particular MRI scanner 55. In some examples, processor 34 of patient programmer 62 is configured to communicate with MRI modality 54 or MRI data server 58 directly, via network 66, or via an intermediary device, e.g., clinician programmer 64, to retrieve MRI compatibility information regarding the particular MRI modality 54.

In examples in which processor 34 determines that AIMD 14 is not compatible with the specific MRI modality 54, processor 34 may output an indication that AIMD 14 is incompatible with the MRI modality 54 and the MRI scan is refused (88). For example, processor 34 may direct a display or other user interface medium to convey such an indication to a user in a visible, audible or other effective manner. In some examples, processor 34 may transmit the notification to another computing device in system 50, e.g., patient information terminal 52, MRI modality 54, MRI compatibility web server 68, or the like, which then displays the notification to a user, such as patient 12, a clinician, or an MRI technician. In some examples, processor 34 may not determine that AIMD 14 is incompatible with MRI modality 54, but the MRI compatibility information that processor 34 uses to make the compatibility determination may be incomplete, unclear, or conflicting. In these cases, processor 34 may alert a user of the questionable information, and may refuse to authorize an MRI scan until the information is corrected or provided.

In some examples, instead of processor 34 making the determination of compatibility between AIMD 14 and an MRI modality 54, processor 34 may transmit the collected MRI compatibility information to another computing device in system 50, which then makes the compatibility determination. In some examples, the other computing device may be patient information terminal 52, MRI modality 54, or MRI compatibility web server 68.

In some examples, processor 34 optionally may proceed to confirm that AIMD 14 comprises MRICS or MRIS hardware (76). Processor 34 of patient programmer 62 may confirm that the AIMD 14 comprises MRICS or MRIS hardware by collecting information including, for example, the implant date of AIMD 14, the model number, registration number, or serial number of AIMD 14 and/or leads 16, or the like. In some example, processor 34 may have obtained at least some of this information when obtaining MRI compatibility information (112), while in other examples, processor 34 may obtain at least some of the information from memory 26 of AIMD 14 and/or memory 36 of patient programmer 62 at this time. In some examples, processor 34 may utilize the implant date as a sort of threshold qualification in determining whether the implant comprises MRICS or MRIS hardware. For example, it may be known that an AIMD 14 implanted prior to a certain date would not have included MRICS or MRIS hardware. In some examples, processor 34 may utilize the serial number, registration number, or model number of AIMD 14 and leads 16 to retrieve information regarding AIMD 14 or leads 16 from an AMD data server 60, a manufacturer's website, a third party website, or the like. In some examples, as described above, processor 34 may execute pattern recognition algorithm to determine based on a serial number, registration number, or model number whether AIMD 14 and/or leads 16 comprise MRICS or MRIS hardware.

Processor 34 may also use a software lockout check to confirm that AIMD 14 comprises MRICS or MRIS hardware. In some examples, upon implantation of AIMD 14 and leads 16, an implanting physician or another user may communicate the serial number of AIMD 14, serial number of leads 16, and the implant location to a manufacturer of AIMD 14 or a third party, such as a third party that maintains MRICS information for various AIMDs. The manufacturer or third party may determine whether the system is MRICS based on the serial numbers and the implant location. In some examples, the manufacturer or third party may issue a MRICS indication to the implanting physician or a managing physician that indicates that AIMD 14 and leads 16 do or do not form an MRICS or an MRIS system. The implanting physician or managing physician may then program a positive or a negative MRICS or MRIS indication in AIMD 14 and/or patient programmer 62, which is stored in memory 26 of AIMD 14 and/or memory 36 of patient programmer 62. The software lockout check, then, may include obtaining this information from memory 26 of AIMD 14 and/or memory 36 of patient programmer 62. When processor 34 of patient programmer 62 determines that AIMD 14 does not comprise MRICS or MRIS hardware, processor 34 may generate a notification via user interface 38 that AIMD 14 is not compatible with the MRI modality 54 and patient 12 will not undergo an MRI scan (88).

When processor 34 determines that AIMD 14 does, in fact, comprise MRICS or MRIS hardware, processor 34 optionally may proceed to analyze the implant location of AIMD 14 and/or leads 16 and any MRICS hardware exceptions (78) as another safety check. In some examples, the implant location of AIMD 14 and/or leads 16 or MRICS hardware exceptions may be stored in memory 26 of AIMD 14 and/or memory 36 of patient programmer 62.

Some locations at which AIMD 14 or leads 16 are implanted may preclude patient 12 from having an MRI scan. For example, leads 16 may be implanted proximate to a particular anatomical target of the patient 12, or near a target that does not correspond to a customary implant location. Similarly, leads 16 that are orphaned, i.e., unconnected to a stimulator, or damaged may preclude patient 12 from having an MRI scan due to potential overheating of tissue adjacent the leads 16. When processor 34 determines that AIMD 14 is implanted in a location that precludes an MRI scan or patient 12 has implanted leads 16 that are damaged or orphaned, processor 34 may generate a notification via user interface 38 to alert a user that patient 12 cannot undergo an MRI scan (88).

Once processor 34 of patient programmer 62 has determined that AIMD 14 is compatible with an MRI modality 54, processor 34 may generate and transmit a command to processor 24 of AIMD 14 to enter a MRI conditionally safe operating mode (118). Processor 24 may switch from a normal operating mode, in which stimulation generator 30 delivers therapy to patient 12 via electrodes carried by leads 16, to the MRI safe operating mode in response to the command received via telemetry circuit 28 from processor 34 of programmer 62. In some examples, in the MRI conditionally safe operating mode, processor 24 may control the components of AIMD 14 to be in a low power mode that provides sufficient functionality to the components, e.g., processor 24 and stimulation generator 30, to prevent stimulation therapy from accidentally being delivered to patient 12 during the MRI scan. In the MRI conditionally safe operating mode, according to some examples, processor 24 of AIMD 14 may remain awake but does not actively deliver electrical stimulation to the patient. In examples in which AIMD 14 is MRI safe, AIMD 14 may not need to be configured in a MRI conditionally safe operating mode, as AIMD 14 is safe for an MRI scan when operating in its normal operating mode.

In addition to causing processor 24 and stimulation generator 30 to enter a low power mode in which therapy is not delivered to patient 12, the MRI conditionally safe operating mode may define certain conditions which must be complied with during the time that AIMD 14 is configured in the MRI conditionally safe operating mode. For example, the MRI conditionally safe operating mode may define a time for which AIMD 14 may be in the MRI conditionally safe operating mode, a position which patient 12 must assume during the time which AIMD 14 is in the MRI conditionally safe operating mode, a power or duration of the MRI scan, or the like. Upon entering MRI conditionally safe operating mode, processor 34 of patient programmer 62 may display the conditions via user interface 38. In some examples, to increase a likelihood that patient 12 or a user, such as an MRI technician, comply with the conditions, processor 34 of patient programmer 62 may display the conditions via user interface 38 and wait for an input or response from patient 12 or the user before entering the MRI safe operating mode.

In some examples, in processor 24 of AIMD 14 may be configured to be able to enter two or more MRI conditionally safe operating modes. In some examples, processor 24 may be configured to enter a first MRI conditionally safe operating mode when MRI modality 54 operates using a first set of operating parameters or comprises a first RF coil type, or when a MRI scan is utilized for a first portion of the body of patient 12 (e.g., a head). Processor 24 then may be configured to enter a second MRI conditionally safe operating mode when MRI modality operates using a second set of operating parameters (e.g., a second magnetic field strength) or comprises a second RF coil type, or when a MRI scan is utilized for a second portion of the body of patient 12 (e.g., a full body MRI scan).

In other examples, processor 24 may be configured to enter the first MRI conditionally safe operating mode when at least one condition for entering the second MRI conditionally safe operating mode is not met. For example, patient 12 may be requesting stimulation or monitoring or a physiological parameter of patient 12 may indicate to processor 24 that stimulation is required. Processor 24 then enter the first MRI conditionally safe operating mode, and processor 34 of programmer 62 may display via user interface 38 a more restrictive set of conditions which must be complied with during the time that AIMD 14 is configured in the MRI conditionally safe operating mode. For example, the more restrictive conditions may include more conservative operating parameters of MRI scanner 55, such as a lower maximum magnetic field. When all conditions are met for entering the MRI safe operating mode, processor 24 may enter the MRI safe operating mode, which may have a less restrictive set of conditions which must be complied with during the time that AIMD 14 is configured in the MRI conditionally safe operating mode. For example, the less restrictive conditions may include less conservative operating parameters of MRI scanner 55, such as a higher magnetic field.

In some examples, the technique may conclude with processor 34 of patient programmer 62 preparing MRI modality 54 for scanning patient 12 (120). Such a step may not be performed by processor 34 of patient programmer 62 in all examples. However, preparing MRI modality 54 via processor 34 of patient programmer 62 may further automate the procedure of determining MRI compatibility of AIMD 14 and preparing AIMD 14 and MRI modality 54 for an MRI scan of patient 12.

As shown in FIG. 4, processor 34 of patient programmer 62 and MRI modality 54 may be connected to a network 66 via which processor 34 may transmit an instruction to MRI modality 54 to prepare for scanning patient 12. Preparation of the MRI modality 54 for scanning may include, for example, scan parameter validation, e.g., setting or confirming MRI scan parameters according to which the MRI scanner 55 will scan patient 12. The MRI scan parameters may include, for example, a magnetic field magnitude and a gradient strength. A magnetic field that is too high may not be suitable for a patient 12 having an AIMD 14 implanted in his or her body, as described above. Similarly, a gradient strength that is too large may not be suitable for a patient having an AIMD 14 implanted in his or her body.

In some examples, the scan parameters determined by processor 34 and communicated via network 66 to MRI modality 54 may be verified by a user, such as a clinician or MRI technician. The user should confirm that the MRI scan parameters adhere to the guidelines of the AIMD 14 implanted in patient 12. In some examples, the user may consult a radiologist or a manufacturer of AIMD 14 for assistance in validating the MRI scan parameters. For example, the user may contact the manufacturer of AIMD 14 via a phone call or a website of the manufacturer.

The user may also validate that the RF coil of the MRI scanner 55 is compatible with AIMD 14. For example, AIMD 14 may be compatible only with an MRI scanner 55 that include a single channel RF coil, and may not be compatible with an MRI scanner 55 that includes a multiple channel RF coil. As another example, a quadrature bird cage RF coil may function in linear mode and cause AIMD 14 to be exposed to an excessive magnetic field.

In some examples, the user may perform a test MRI scan, e.g., an MRI scan that is not performed on patient 12, to ensure proper functioning of the MRI RF coil. If the test scan fails to produce expected image quality or indicates improper operation of the MRI RF coil, the MRI scanner 55 may not be suitable to scan patient 12, and further investigation may be required (90).

In some examples, the MRI scanner 55 may include an AIMD mode that assures stringent internal limits on operation of the MRI scanner 55 to prevent AIMD 14 from being exposed to excessive magnetic fields. Processor 34 communicate an instruction to MRI modality 54 to configure the MRI scanner 55 in the AIMD mode prior to scanning patient 12. Once the MRI scanner 55 is prepared for scanning (120), the user may initiate the MRI scan of patient 12.

In some examples, a processor may implement a technique to make a determination of compatibility between an AIMD 14 and a MRI modality 54 which may include obtaining MRI compatibility information from an external data server (i.e., a data server separate from the computing device which includes the processor). Any of the computing devices described herein may include the processor, such as AIMD 14, external programmer 20, patient information terminal 52, MRI modality 54, MRI compatibility web server 68, MRI data server 58, or AIMD data server 60. In some examples, the external data server may include at least one of patient data archive 56, AIMD data server 60, or MRI data server 58. The processor may access the external data server via network 66. In some examples, the external data server may be located remotely from the processor, e.g., in a different physical location. In some examples, the processor may complement the MRI compatibility information obtained from the data server(s) with information obtained from additional sources, such as MRI compatibility web server 68, AIMD 14, external programmer 20, MRI modality 54, or patient information terminal 52. As described above, the MRI compatibility information may include AIMD information and/or MRI modality information. The processor then may utilize the MRI compatibility in a manner similar to the techniques described herein, such as techniques described with reference to one or more of FIGS. 5-8.

The techniques described in this disclosure, including those attributed to various computing devices or other components of system 50, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, AIMDs, web servers, data servers, information terminals, or other computing devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Many aspects of the disclosure have been described. Various modifications may be made without departing from the scope of the claims. These and other examples are within the scope of the following claims.

What is claimed is:

1. A system comprising a processor configured to:
automatically obtain magnetic resonance imaging (MRI) compatibility information relating to compatibility of an active implantable medical device (AIMD) implantable in a patient with an MRI modality from at least two information sources, wherein the at least two information sources comprise at least one of a first information source associated with a patient programmer or a second information source associated with the AIMD;
automatically determine compatibility of the AIMD with the MRI modality based on the MRI compatibility information; and
in response to a determination that the AIMD is incompatible with the MRI modality, output an indication that the AIMD is incompatible with the MRI modality, wherein the indication is configured to cause a MRI scan to be refused.

2. The system of claim 1, further comprising the at least two information sources.

3. The system of claim 1, wherein one of the at least two information sources comprises the first information source associated with the patient programmer and another of the at least two information sources comprises at least one of a third information source associated with a patient information terminal, a fourth information source associated with a patient data archive, a fifth information source associated with an AIMD data server, a sixth information source associated with an MRI data server, and the second information source associated with the AIMD.

4. The system of claim 1, wherein the processor is further configured to generate a notification indicating whether the AIMD is compatible with the MRI modality based on the determination.

5. The system of claim 1, wherein the processor is further configured to archive in a patient data archive at least one of the MRI compatibility information and the determination of whether the AIMD is compatible with the MRI modality.

6. The system of claim 1, further comprising the AIMD, and wherein the processor automatically instructs the AIMD to enter an MRI conditionally safe operating mode.

7. The system of claim 1, further comprising an external programmer for the AIMD, wherein the processor, via the external programmer, prompts a user to configure the AIMD in an MRI conditionally safe operating mode.

8. The system of claim 1, further comprising a patient information terminal, a data server, and an MRI compatibility web server, wherein one of the patient information terminal, the data server and the MRI compatibility web server comprises the processor.

9. The system of claim 1, wherein the MRI compatibility information comprises an implant location of the AIMD, and wherein the processor is further configured to confirm whether the implant location of the AIMD permits an MRI scan to be performed by the MRI modality.

10. A method comprising:
automatically obtaining with a processor magnetic resonance imaging (MRI) compatibility information relating to compatibility of an active implantable medical device (AIMD) implantable in a patient with an MRI modality from at least two information sources, wherein the at least two information sources comprise at least one of a first information source associated with a patient programmer or a second information source associated with the AIMD, wherein the patient programmer is configured to communicate with the AIMD;
automatically determining with the processor compatibility of the AIMD with the MRI modality based on the MRI compatibility information; and
in response to a determination that the AIMD is incompatible with the MRI modality, outputting, with the processor, an indication that the AIMD is incompatible with the MRI modality, wherein the indication is configured to cause a MRI scan to be refused.

11. The method of claim 10, wherein automatically obtaining with the processor MRI compatibility information comprises automatically obtaining with the processor the MRI compatibility information from the first information source associated with the patient programmer and at least one of a third information source associated with a patient information terminal, a fourth information source associated with a patient data archive, a fifth information source associated with an AIMD data server, a sixth information source associated with an MRI data server, and the second information source associated with the AIMD.

12. The method of claim 10, further comprising automatically generating with the processor a notification indicating whether the AIMD is compatible with the MRI modality based on the determination.

13. The method of claim 10, further comprising automatically archiving in a patient data archive at least one of the MRI compatibility information and the determination of whether the AIMD is compatible with the MRI modality.

14. The method of claim 10, further comprising automatically instructing the AIMD to enter an MRI conditionally safe operating mode.

15. The method of claim 10, further comprising prompting, via an external programmer for the AIMD, a user to configure the AIMD in an MRI conditionally safe operating mode.

16. The method of claim 10, wherein the MRI compatibility information comprises an implant location of the AIMD, the method further comprising:
confirming with the processor whether the implant location of the AIMD permits an MRI scan to be performed by the MRI modality.

17. A computer-readable medium comprising instructions that cause a processor to:
automatically obtain magnetic resonance imaging (MRI) compatibility information relating to compatibility of an active implantable medical device (AIMD) implantable in a patient with an MRI modality from at least two information sources, wherein the at least two information sources comprise at least one of a first information source associated with a patient programmer or a second information source associated with the AIMD, wherein the patient programmer is configured to communicate with the AIMD;

automatically determine compatibility of the AIMD with the MRI modality based on the MRI-compatibility information; and in response to a determination that the AIMD is incompatible with the MRI modality, output an indication that the AIMD is incompatible with the MRI modality, wherein the indication is configured to cause a MRI scan to be refused.

18. The computer-readable medium of claim 17, further comprising instructions that cause the processor to automatically generate a notification indicating whether the AIMD is compatible with the MRI modality based on the determination.

19. The computer-readable medium of claim 17, further comprising instructions that cause the processor to automatically archive in a patient data archive at least one of the MRI compatibility information and the determination of whether the AIMD is compatible with the MRI modality.

20. The computer-readable medium of claim 17, further comprising instructions that cause the processor to automatically instruct the AIMD to enter an MRI conditionally safe operating mode.

21. The computer-readable medium of claim 17, further comprising instructions that cause the processor to prompt, via an external programmer for the AIMD, a user to configure the AIMD in an MRI conditionally safe operating mode.

22. The computer-readable medium of claim 17, wherein the MRI compatibility information comprises an implant location of the AIMD, and the computer-readable medium further comprises instruction that cause the processor to:

confirm whether the implant location of the AIMD permits an MRI scan to be performed by the MRI modality.

23. A system comprising:

means for automatically obtaining magnetic resonance imaging (MRI) compatibility information relating to compatibility of an active implantable medical device (AIMD) implantable in a patient with an MRI modality from at least two information sources, wherein the at least two information sources comprise at least one of a first information source associated with a patient programmer or a second information source associated with the AIMD, wherein the patient programmer is configured to communicate with the AIMD;

means for automatically determining compatibility of the AIMD with the MRI modality based on the MRI compatibility information; and means for, in response to a determination that the AIMD is incompatible with the MRI modality, outputting an indication that the AIMD is incompatible with the MRI modality, wherein the indication is configured to cause a MRI scan to be refused.

24. The system of claim 23, wherein the MRI compatibility information comprises an implant location of the AIMD, further comprising:

means for confirming whether the implant location of the AIMD permits an MRI scan to be performed by the MRI modality.

* * * * *